(12) United States Patent
Jiang

(10) Patent No.: US 11,701,520 B2
(45) Date of Patent: Jul. 18, 2023

(54) HERMETIC FEEDTHROUGH ASSEMBLY AND ASSOCIATED METHODS

(71) Applicant: Pacesetter, Inc., Sylmar, CA (US)

(72) Inventor: Xiaofei Jiang, Clemson, SC (US)

(73) Assignee: Pacesetter, Inc., Sylmar, CA (US)

( * ) Notice: Subject to any disclaimer, the term of this patent is extended or adjusted under 35 U.S.C. 154(b) by 328 days.

(21) Appl. No.: 16/869,760

(22) Filed: May 8, 2020

(65) Prior Publication Data
US 2021/0346705 A1 Nov. 11, 2021

(51) Int. Cl.
| | |
|---|---|
| *A61N 1/378* | (2006.01) |
| *A61N 1/375* | (2006.01) |
| *A61N 1/39* | (2006.01) |
| *H01M 50/10* | (2021.01) |
| *H01M 50/172* | (2021.01) |
| *A61B 5/283* | (2021.01) |

(52) U.S. Cl.
CPC ............ *A61N 1/3787* (2013.01); *A61B 5/283* (2021.01); *A61N 1/3756* (2013.01); *A61N 1/37512* (2017.08); *A61N 1/3956* (2013.01); *H01M 50/10* (2021.01); *H01M 50/172* (2021.01); *A61B 2560/0214* (2013.01); *A61B 2562/125* (2013.01); *A61B 2562/16* (2013.01); *H01M 2220/30* (2013.01)

(58) Field of Classification Search
CPC .............. A61N 1/3787; A61N 1/37512; A61N 1/3756; A61N 1/3956; A61N 1/3754; H01M 50/172; H01M 50/10; H01M 2220/30; A61B 5/283; A61B 2560/0214; A61B 2562/125; A61B 2562/16
See application file for complete search history.

(56) References Cited

U.S. PATENT DOCUMENTS

| | | | |
|---|---|---|---|
| 2009/0079517 A1* | 3/2009 | Iyer | ......................... H01G 2/04 333/182 |
| 2011/0015694 A1 | 1/2011 | Alexander et al. | |
| 2018/0138463 A1 | 5/2018 | Bruch et al. | |

* cited by examiner

*Primary Examiner* — Tammie K Marlen
(74) *Attorney, Agent, or Firm* — Dean D. Small; The Small Patent Law Group, LLC

(57) ABSTRACT

An implantable medical device, battery and method include memory configured to store program instructions. At least one of circuitry or a processor are configured to execute the program instructions in connection with at least one of monitoring a biological signal or administering a therapy. The device includes a battery comprising a cell stack that includes an anode, a cathode, and one or more separator layers electrically insulating the anode from the cathode. The device includes a case having a feedthrough port and a feedthrough assembly disposed in the feedthrough port. The feedthrough assembly includes a ferrule having a lumen. An inner conductor is disposed within the lumen of the ferrule. The inner conductor is formed from a material having a first composition and a first coefficient of thermal expansion (CTE). An insulating core is disposed within the lumen of the ferrule and separates the inner conductor from the ferrule. The insulating core is formed from a material having a second composition and a second CTE. The first CTE of the inner conductor is equal to or greater than the second CTE of the insulating core and the first and second compositions are molecularly bonded with one another to form a hermetic seal between the inner conductor and the insulating core.

20 Claims, 13 Drawing Sheets

HERMETIC FEEDTHROUGH ASSEMBLY AND ASSOCIATED METHODS

BACKGROUND

Embodiments of the present disclosure generally relate to hermetic feedthrough assemblies and associated methods.

Batteries used in implantable medical devices (IMDs), such as cardiac pacemakers and implantable cardiac monitors (ICMs), are required to meet high quality and performance specifications and reliability. They need to have high energy density, high rate capability and long shelf life. Since replacement of the battery of an IMD means that the patient must undergo surgery, batteries for IMDs must have a long service life. Improvement to the reliability, performance, and lifetime of such batteries is highly desirable.

Lithium batteries are commonly implemented in IMDs. Some examples of types of lithium batteries used in IMDs include lithium/iodine batteries, lithium/thionyl chloride batteries, lithium/manganese dioxide batteries, lithium/carbon monofluoride batteries, lithium/silver vanadium oxide (SVO) batteries, batteries including hybrid cathode systems based on SVO in conjunction with carbon monofluoride, and the like. Lithium batteries used in IMDs may include types of rechargeable lithium batteries. The internal components of a lithium battery are sensitive to moisture and need to be hermetically sealed against moisture ingress. Conversely, leakage of corrosive components outside of the case may damage other IMD components, leading to improper functioning or failure of the IMD. Accordingly, a lithium battery for an IMD includes a hermetically sealed metal case to isolate the internal components of the battery from the other IMD components.

A feedthrough assembly is provided in the hermetically sealed case to facilitate electrical connection between the lithium battery and the circuitry of the IMD, while maintaining the hermetic seal between the battery and other IMD components. The hermetic feedthrough assembly may be a compression glass-to-metal seal (GTMS) feedthrough. A hermetic compression GTMS feedthrough may include a metal ferrule having a lumen, at least one pin or conductor, and a glass insulator separating the ferrule from the molybdenum pin. In a hermetic compression GTMS feedthrough, the coefficient of thermal expansion (CTE) of the ferrule is greater than the glass insulator and the CTE of the glass insulator is greater than the pin. The positive pressure exerted by the ferrule on the glass insulator and by the glass insulator on the pin achieves the hermetic compression seal of the feedthrough assembly. Molybdenum is usually selected as the pin material because it has a CTE that may be readily matched to suitable metal ferrule and glass insulator materials to form a hermetic compression seal and exhibits good corrosion resistance to lithium battery materials. Molybdenum also exhibits good electrical conductivity, which is important in high current battery applications (e.g. 1 or more amperes). For example, a compressive hermetic GTMS seal may include a ferrule formed from stainless steel 340L (e.g., having a CTE of $10 \times 10^{-6}$/° C.), a glass insulator formed from calcium-boro-aluminate-12 (CABAL-12) glass (e.g., having a CTE of $6 \times 10^{-6}$/° C.), and a pin formed from molybdenum (e.g., having a CTE of $5 \times 10^{-6}$/° C.). However, joining molybdenum pins to other battery and/or IMD components presents several challenges to forming reliable electrical connections. For example, molybdenum has a melting temperature of 4,753° F. (2,623° C.), requiring welding (e.g., via laser welding) at temperatures that may create stress in the glass insulator during the welding operation. Accordingly, a need remains for a feedthrough assembly that affords more reliable electrical connections to other battery and/or IMD components and/or avoids damage to other components of the feedthrough assembly during joining operations to establish electrical connections.

SUMMARY

In accordance with embodiments herein, an implantable medical device is provided. The implantable medical device includes memory configured to store program instructions. At least one of circuitry or a processor are configured to execute the program instructions in connection with at least one of monitoring a biological signal or administering a therapy. The implantable medical device includes a battery comprising a cell stack that includes an anode, a cathode, and one or more separator layers electrically insulating the anode from the cathode. The implantable medical device includes a case having a feedthrough port and a feedthrough assembly disposed in the feedthrough port. The feedthrough assembly includes a ferrule having a lumen. An inner conductor is disposed within the lumen of the ferrule. The inner conductor is formed from a material having a first composition and a first coefficient of thermal expansion (CTE). An insulating core is disposed within the lumen of the ferrule and separates the inner conductor from the ferrule. The insulating core is formed from a material having a second composition and a second CTE. The first CTE of the inner conductor is equal to or greater than the second CTE of the insulating core and the first and second compositions are molecularly bonded with one another to form a hermetic seal between the inner conductor and the insulating core.

Optionally, the case may represent a battery case. The battery case and feedthrough assembly may hermetically enclose the cell stack. The inner conductor may have a first end connected to one of the anode and the cathode. The inner conductor may have a second end connected to at least one of the circuitry or the processor. The device may further comprise a housing that further encloses the memory, processor and the battery case. The case may represent a housing for the implantable medical device. The case and feedthrough assembly may hermetically enclose the memory, the battery and at least one of the circuitry or the processor. The device may further comprise a header configured to be coupled to one or more leads. The header may be mounted to the housing proximate the feedthrough assembly. The inner conductor may have a first end connected to at least one of the circuitry or the processor. The inner conductor may have a second end configured to be connected to at least one of an antenna or an electrode.

Optionally, the insulating core may not form a compression hermetic seal to the inner conductor due, at least in part, to the first CTE being equal to or greater than the second CTE. The material forming the inner conductor may have a melting point at or below 4500° F. The inner conductor may be formed from at least one of titanium or niobium. The inner conductor and the ferrule may be made of a common material. The first composition of the inner conductor may represent an oxide based composition and the second composition of the insulating core represents an oxide based composition. The molecular bond may represent a chemical bond between the oxide based compositions of the first and second compositions to form the hermetic seal. The cathode may include a current collector disposed between cathode blanks. The current collector and the inner conductor may be made of a common material.

In accordance with embodiments herein, a battery is provided. The battery includes a case having a feedthrough port. A cell stack is disposed within the case. The cell stack includes an anode, a cathode, and one or more separator layers electrically insulating the anode from the cathode. A feedthrough assembly is disposed in the feedthrough port. The feedthrough assembly include a ferrule having a lumen. An inner conductor is disposed within the lumen of the ferrule. The inner conductor is formed from a material having a first composition and a first coefficient of thermal expansion (CTE). An insulating core is disposed within the lumen of the ferrule and separating the inner conductor from the ferrule. The insulating core is formed from a material having a second composition and a second CTE. The first CTE of the inner conductor is equal to or greater than the second CTE of the insulating core and the first and second compositions are molecularly bonded with one another to form a hermetic seal between the inner conductor and the insulating core.

Optionally, the insulating core may not form a compression hermetic seal to the inner conductor due, at least in part, to the first CTE being equal to or greater than the second CTE. The material forming the inner conductor may have a melting point at or below 4500° F. The inner conductor may be formed from at least one of titanium or niobium. The inner conductor and the ferrule may be made of a common material. The first composition of the inner conductor may represent an oxide based composition and the second composition of the insulating core may represent an oxide based composition. The molecular bond may represent a chemical bond between the oxide based compositions of the first and second compositions to form the hermetic seal.

In accordance with embodiments herein, a method is provided. The method disposes a cell stack within a case. The cell stack includes an anode, a cathode, and one or more separator layers electrically insulating the anode from the cathode. The case has a feedthrough port. The method forms a feedthrough assembly that includes a ferrule having a lumen. The forming includes disposing an inner conductor within the lumen of the ferrule. The inner conductor is formed from a material having a first composition and a first coefficient of thermal expansion (CTE). The method disposes an insulating core within the lumen of the ferrule and separating the inner conductor from the ferrule. The insulating core is formed from a material having a second composition and a second CTE. The first CTE of the inner conductor is equal to or greater than the second CTE of the insulating core. The first and second compositions are molecularly bonded with one another to form a hermetic seal between the inner conductor and the insulating core and inserts the feedthrough assembly in the feedthrough port.

Optionally, the case may represent a battery case. The battery case and feedthrough assembly may hermetically enclose the cell stack, and may further comprise connecting a first end of the inner conductor to one of the anode and the cathode, connecting a second end of the inner conductor to at least one of a circuitry or a processor of an implantable medical device and disposing the memory, processor and the battery case in a housing of the implantable medical device. The case may represent a housing for an implantable medical device. The case and feedthrough assembly may hermetically enclose a memory, a battery and at least one of the circuitry or the processor and may further comprise mounting a header to the housing proximate the feedthrough assembly, the header configured to be coupled to one or more leads, connecting a first end of the inner conductor to at least one of the circuitry or the processor and connecting a second end of the inner conductor to at least one of an antenna or an electrode. The material forming the inner conductor may have a melting point at or below 4500° F. The feedthrough assembly may further comprise forming the inner conductor and one or more of the ferrule and a current collector of the anode from a common material.

DETAILED DESCRIPTION

Figure 1:
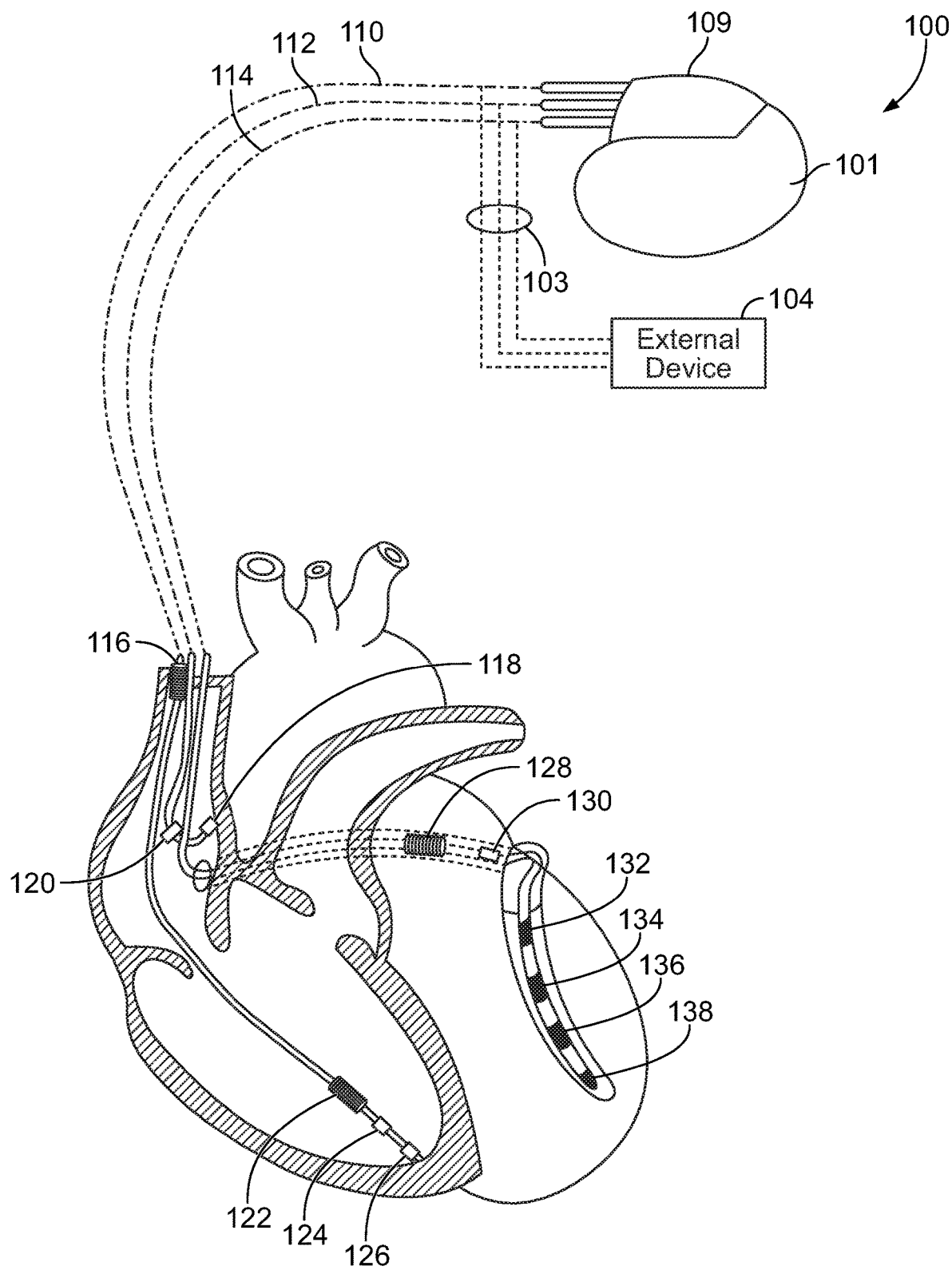
FIG. 1 illustrates an IMD and external device coupled to a heart in a patient and implemented in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

System Overview

Embodiments herein include systems, devices, and methods of providing hermetic feedthrough assemblies. Such systems, devices, and methods may be implemented in a battery case and/or an IMD housing. The hermetic feedthrough assembly (or header) may be disposed in a feedthrough port of the case or housing. The feedthrough assembly includes a ferrule having a lumen, an inner conductor disposed within the lumen, and an insulating core disposed between the lumen and the inner conductor. Optionally, the ferrule may define at least two lumens and the feedthrough assembly may include an inner conductor disposed in each corresponding one of the at least two lumens. The feedthrough assembly may be glass-to-metal seal (GTMS) feedthrough. Titanium (e.g., grade 1 titanium, grade 2 titanium, or the like) may be used to form both the ferrule and the inner conductor. The insulating core may be formed from a low silica or silica-free insulating glass (e.g., Ta-23, CABAL-12, or the like). The coefficient of thermal expansion (CTE) of both the ferrule and the inner conductor (e.g., titanium having a CTE of about $9 \times 10^{-6}/° C$. are greater than the insulating core (e.g., CABAL-12 having a CTE of $6 \times 10^{-6}/° C$.). Accordingly, the insulating core does not form a compression hermetic seal to the inner conductor because the CTE of the insulating core is greater than the CTE of the inner conductor. Rather, the hermetic seal of the feedthrough assembly is formed, at least in part, by molecular bonding that occurs between the insulating core and the inner conductor. The molecular bonding is facilitated by the good wettability of the insulating glass by the titanium during a GTMS production process (e.g., including heating the feedthrough assembly to melt and flow the insulating core and cooling the feedthrough assembly to re-solidify the insulating core). The titanium ferrule and inner conductor exhibit good weldability to other battery and IMD components compared to higher melting point refractory metals (e.g., molybdenum, or the like). For example, the titanium ferrule and inner conductor may only require resistance welding (e.g., versus laser welding for molybdenum) to the internal battery stack, the case, and/or the IMD circuitry. The titanium inner conductor may also be desirable in low to medium current battery applications due to the reduced voltage drop across the inner conductor.

Additionally or alternatively, embodiments herein provide for the inner conductor, the ferrule, and/or the case to be made of or include a common material. The common material may be titanium or a titanium alloy. Such embodiments may be desirable in some batteries (e.g., lithium batteries) implemented in low to medium current battery applications (e.g. microamperes to milliamperes). Low to medium current battery applications for IMDs may include cardiac pacemakers, ICMs, and the like. The common material (e.g., titanium or a titanium alloy) may offer increased biocompatibility of the battery case and/or the IMD housing.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference in their entireties.

Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference in their entireties. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference in their entireties.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties.

Additionally or alternatively, the IMD may be a leadless cardiac monitor (ICM) that includes one or more structural and/or functional aspects of the device(s) described in U.S. patent application Ser. No. 15/084,373, filed Mar. 29, 2016, entitled, "Method And System To Discriminate Rhythm Patterns In Cardiac Activity," which is hereby incorporated by reference in its entirety. Additionally or alternatively, the IMD may be an ICM that includes one or more structural and/or functional aspects of the device(s) and/or method(s) described in U.S. patent application Ser. No. 15/973,126, titled "Method And System For Second Pass Confirmation Of Detected Cardiac Arrhythmic Patterns"; U.S. patent application Ser. No. 15/973,351, titled "Method And System To Detect R-Waves In Cardiac Arrhythmic Patterns"; U.S. patent application Ser. No. 15/973,307, titled "Method And System To Detect Post Ventricular Contractions In Cardiac Arrhythmic Patterns"; and U.S. patent application Ser. No. 16/399,813, titled "Method And System To Detect Noise In Cardiac Arrhythmic Patterns".

Additionally or alternatively, the IMD may be a passive implantable medical device (PIMD). Non-limiting examples of PIMDs may include passive wireless sensors used by themselves, or incorporated into or used in conjunction with other implantable medical devices (IMDs) such as cardiac monitoring devices, pacemakers, cardioverters, cardiac rhythm management devices, defibrillators, neurostimulators, leadless monitoring devices, leadless pacemakers, replacement valves, shunts, grafts, drug elution devices, blood glucose monitoring systems, orthopedic implants, and the like. For example, the PIMD may include one or more structural and/or functional aspects of the device(s) described in U.S. Pat. No. 9,265,428 entitled "Implantable Wireless Sensor", U.S. Pat. No. 8,278,941 entitled "Strain Monitoring System and Apparatus", U.S. Pat. No. 8,026,729 entitled "System and Apparatus for In-Vivo Assessment of Relative Position of an Implant", U.S. Pat. No. 8,870,787 entitled "Ventricular Shunt System and Method", and U.S. Pat. No. 9,653,926 entitled "Physical Property Sensor with Active Electronic Circuit and Wireless Power and Data Transmission", which are all hereby incorporated by reference in their respective entireties.

Additionally or alternatively, the IMD may be a body generated analyte test device or "BGA test device". Non-limiting examples of BGA test devices include equipment, devices, disposable products utilized to collect and analyze a BGA. The BGA test device may implement one or more of the methods, devices and systems described in the following publications, all of which are incorporated herein by reference in their entireties: U.S. Patent Publication Number 2011/0256024, entitled "MODULAR ANALYTE MONITORING DEVICE", published Oct. 20, 2011; U.S. Patent Publication Number 2010/0198142, entitled "MULTI-FUNCTION ANALYTE TEST DEVICE AND METHODS THEREFORE", published Aug. 5, 2010; U.S. Patent Publication Number 2011/0160544, entitled "SYSTEM AND METHOD FOR ANALYSIS OF MEDICAL DATA TO ENCOURAGE HEALTHCARE MANAGEMENT", published Jun. 30, 2011; U.S. Pat. No. 5,063,081, entitled "METHOD OF MANUFACTURING A PLURALITY OF UNIFORM MICROFABRICATED SENSING DEVICES HAVING AN IMMOBILIZED LIGAND RECEPTOR" issued Nov. 5, 1991; U.S. Pat. No. 7,419,821, entitled "APPARATUS AND METHODS FOR ANALYTE MEASUREMENT AND IMMUNOASSAY" issued Sep. 2, 2008; U.S. Patent Publication Number 2004/0018577, entitled "MULTIPLE HYBRID IMMUNOASSAYS" published Jan. 29, 2004; U.S. Pat. No. 7,682,833, entitled "IMMUNOASSAY DEVICE WITH IMPROVED SAMPLE CLOSURE" issued Mar. 23, 2010; U.S. Pat. No. 7,723,099, entitled "IMMUNOASSAY DEVICE WITH IMMUNO-REFERENCE ELECTRODE" issued May 25, 2010.

Further, one or more combinations of IMDs may be utilized from the above incorporated patents and applications in accordance with embodiments herein. All references, including publications, patent applications and patents, cited herein are hereby incorporated by reference to the same extent as if each reference were individually and specifically indicated to be incorporated by reference and were set forth in its entirety herein.

FIG. 1 illustrates an IMD 100 and external device 104 coupled to a heart in a patient and implemented in accordance with embodiments herein. The external device 104 may be a programmer, an external defibrillator, a workstation, a portable computer, a personal digital assistant, a cell phone, a bedside monitor, or the like. The IMD 100 may represent a cardiac monitoring device, pacemaker, cardioverter, cardiac rhythm management device, defibrillator, neurostimulator, leadless monitoring device, leadless pacemaker or the like, implemented in accordance with one embodiment of the present invention. The IMD 100 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The IMD 100 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structures for the IMD 100 are discussed and illustrated in the drawings herewith.

The IMD 100 includes a device housing 101 that is joined to a header assembly 109 that holds receptacle connectors connected to one or more of a right ventricular lead 110, a right atrial lead 112, and a coronary sinus lead 114, or the like. The leads 112, 114 and 110 measure cardiac signals of the heart. The right atrial lead 112 includes an atrial tip electrode 118 and an atrial ring electrode 120. The coronary sinus lead 114 includes a left atrial ring electrode 128, a left atrial coil electrode 130 and one or more left ventricular electrodes 132-138 (e.g., also referred to as P1, M1, M2 and D1) to form a multi-pole LV electrode combination. The right ventricular lead 110 includes an RV tip electrode 126, an RV ring electrode 124, an RV coil electrode 122, and an SVC coil electrode 116. The leads 112, 114 and 110 detect IEGM signals that are processed and analyzed as described herein. The leads 112, 114 and 110 also delivery therapies as described herein. The device housing 101 (or case) may include a feedthrough port. A hermetic feedthrough assembly is disposed in the feedthrough port. The hermetic feedthrough assembly includes one or more internal conductors extending therethrough for establishing electrical connection between the internal components of the battery IMD 100 and other components external to the IMD housing (e.g., the header assembly 109). Details of the case and feedthrough assembly are discussed in detail below.

During implantation, the external device 104 is connected to one or more of the leads 112, 114 and 110 through temporary inputs 103. The inputs 103 of the external device 104 receive IEGM signals from the leads 112, 114 and 110 during implantation and display the IEGM signals to the physician on a display. Optionally, the external device 104 may not be directly connected to the leads 112, 114 and 110. Instead, the IEGM cardiac signals sensed by the leads 112, 114 and 110 may be collected by the IMD 100 and transmitted wirelessly to the external device 104. Hence, the external device 104 receives the IEGM cardiac signals through telemetry circuit inputs. The physician or another user controls operation of the external device 104 through a user interface.

Implantable Medical Device

Figure 2:
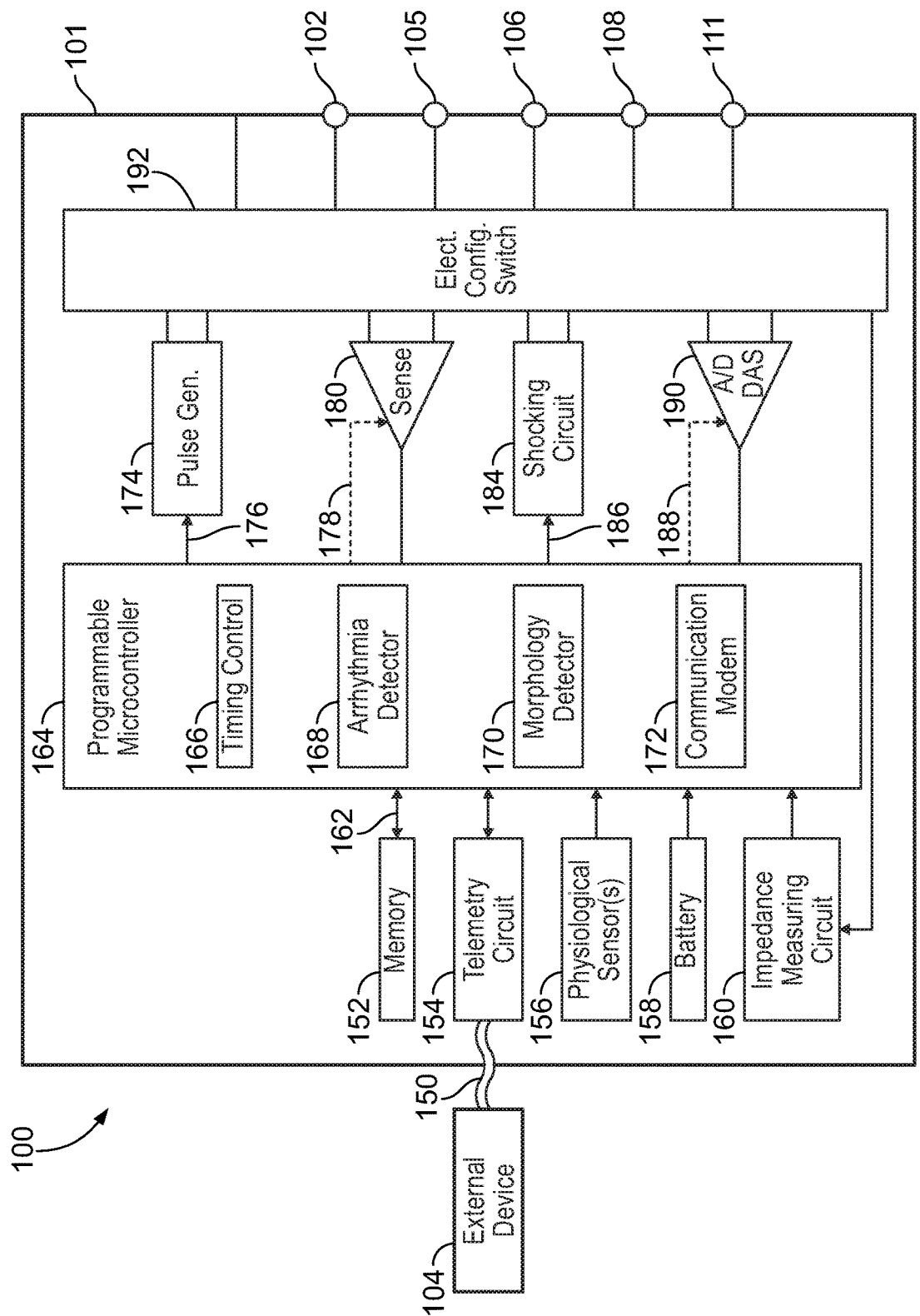
FIG. 2 illustrates a block diagram of the IMD of FIG. 1 in accordance with embodiments herein.

FIG. 2 illustrates a block diagram of the IMD 100 of FIG. 1 in accordance with embodiments herein. The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components. For instance, the IMD may be implemented without ventricular sensing and pacing.

The IMD 100 has a device housing 101 to hold the electronic/computing components. The device housing 101 (which is often referred to as the "can", "case", "encasing", or "case electrode") may be programmably selected to act as the return electrode for certain stimulus modes. The device housing 101 further includes a connector (not shown) with a plurality of terminals 102, 105, 106, 108, and 111. The terminals may be connected to electrodes that are located in various locations within and about the heart.

The IMD 100 includes a programmable microcontroller 164 that controls various operations of the IMD 100, including cardiac monitoring and stimulation therapy. Microcontroller 164 includes one or more microprocessors or CPUs (or equivalent control circuitry), RAM and/or ROM memory, logic and timing circuitry, state machine circuitry, and I/O circuitry. The IMD 100 further includes a first chamber pulse generator 174 that generates stimulation pulses for delivery by one or more electrodes coupled thereto. The pulse generator 174 may deliver pacing pulses and/or anti-tachy pacing therapy. The pulse generator 174 is controlled by the microcontroller 164 via control signal 176. The pulse generator 174 is coupled to the select electrode(s) via an electrode configuration switch 192, which includes multiple switches for connecting the desired electrodes to the appropriate I/O circuits, thereby facilitating electrode programmability.

The microcontroller 164 includes timing control circuitry 166 to control the timing of the stimulation pulses (e.g., pacing rate, atrio-ventricular (AV) delay, atrial interconduction (A-A) delay, or ventricular interconduction (V-V) delay, etc.). The timing control circuitry 166 may also be used for the timing of refractory periods, blanking intervals, noise detection windows, evoked response windows, alert intervals, marker channel timing, and so on. Microcontroller 164 also has an arrhythmia detector 168 for detecting arrhythmia conditions, and a morphology detector 170 to review and analyze one or more features of the morphology of cardiac signals. The IMD 100 is equipped with a communication modem (modulator/demodulator) 172 to enable wireless communication with other devices, implanted devices and/or external devices. In one implementation, the communication modem 172 may use high frequency modulation of a signal transmitted between a pair of electrodes. In one implementation, the communication modem 172 uses high frequency modulation, for example using RF, Bluetooth, or Bluetooth Low Energy telemetry protocols.

The IMD 100 includes sensing circuitry 180 selectively coupled to one or more electrodes that is configured to obtain biological signals (e.g., cardiac activity signals, neurological activity signals, and the like) indicative of biological behavior of an anatomy of interest over a period of time. For example, the sensing circuitry 180 performs sensing operations through the switch 192 to detect the presence of cardiac activity in the right chambers of the heart. The IMD 100 further includes an analog-to-digital (A/D) data acquisition system (DAS) 190 coupled to one or more electrodes via the switch 192 to sample cardiac signals across any pair of desired electrodes. The data acquisition system 190 is configured to acquire intracardiac electrogram signals, convert the raw analog data into digital data, and store the digital data for later processing and/or telemetric transmission to an external device 104 (e.g., a programmer, local transceiver, or a diagnostic system analyzer). The data acquisition system 190 is controlled by a control signal 188 from the microcontroller 164.

The microcontroller 164 is coupled to a memory 152 by a suitable data/address bus 162. The programmable operating parameters used by the microcontroller 164 are stored in memory 152 and used to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The IMD 100 may further include one or more physiologic sensors 156. Such sensors are commonly referred to as "rate-responsive" sensors because they are typically used to adjust pacing stimulation rates according to the exercise state of the patient. However, the physiological sensor 156 may further be used to detect changes in cardiac output, changes in the physiological condition of the heart, or diurnal changes in activity (e.g., detecting sleep and wake states). Examples of physiologic sensors might include sensors that, for example, sense respiration rate, pH of blood, ventricular gradient, activity, position/posture, minute ventilation (MV), and so forth.

A battery 158 provides operating power to all of the components in the IMD 100. The battery 158 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 158 also desirably has a predictable discharge characteristic so that elective replacement time can be detected. As one example, the IMD 100 employs lithium/silver vanadium oxide batteries. The battery 158 includes a cell stack that includes an anode (or anode assembly), a cathode (or cathode assembly), and one or more separator layers electrically insulating the anode from the cathode. The battery is disposed in a case having a feedthrough port (or a header port). A hermetic feedthrough assembly is disposed in the feedthrough port. The hermetic feedthrough assembly includes one or more internal conductors extending therethrough for establishing electrical connection between the internal components of the battery 158 and other IMD components (e.g., the IMD circuitry). Additionally or alternatively, the battery 158 may be a rechargeable battery. Details of the battery and feedthrough assembly are discussed in detail below.

Optionally, the IMD 100 further includes an impedance measuring circuit 160, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Optionally, the microcontroller 164 further controls a shocking circuit 184 by way of a control signal 186. The shocking circuit 184 generates shocking pulses of low (e.g., up to 0.5 joules), moderate (e.g., 0.5-10 joules), or high energy (e.g., 11 to 40 joules), as controlled by the microcontroller 164.

It is recognized that the configurations of circuitry and microcontrollers illustrated herein are by way of example only. Optionally, operations described in connection with the microcontroller may be implemented by circuitry (e.g., firmware and/or discrete circuitry). Optionally, operations described in connection with the circuitry (e.g., firmware and/or discrete circuitry) may be implemented by the microcontroller.

Battery Structure Overview

Figure 3:
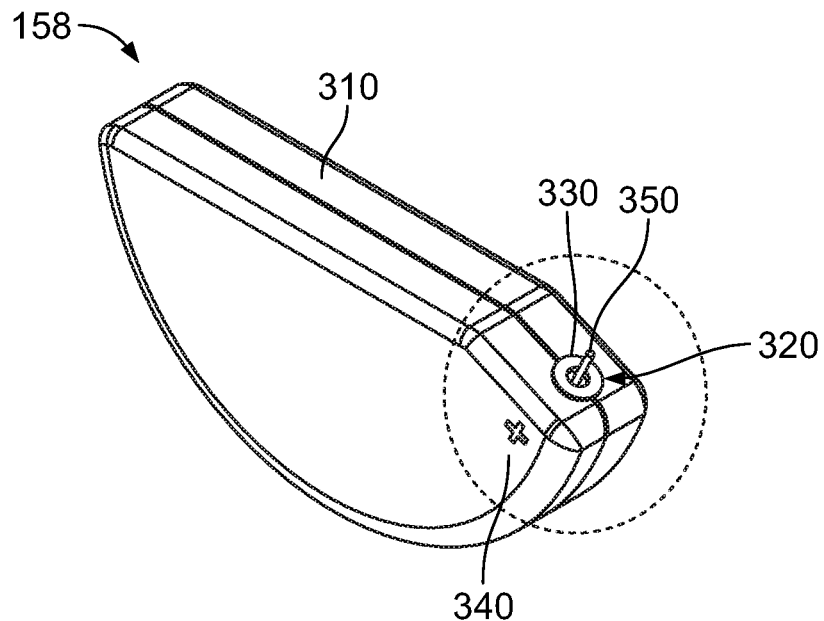
FIG. 3 illustrates a perspective view of an example battery for an IMD in accordance with embodiments herein.

FIG. 3 illustrates a perspective view of an example battery for an IMD in accordance with embodiments herein. The battery 158 includes a case 310 having a feedthrough port 320. A feedthrough assembly 330 may be disposed in the feedthrough port 320. As shown in FIG. 3, a "plus" sign, denoted by "+", on the case 310 indicates that pin 350 is the positive terminal, or cathode terminal. The anode of battery 158 is electrically connected to the case 310, making the case 310 an anode terminal 340 of the battery 158. The plus sign may be engraved, painted, inscribed, or printed on the outer surface of case 310. In some embodiments, according to the disclosure, a cathode pin 350 extends outwardly from the case 310 of the battery 158 in a manner such that an external load such as a cardiac pacemaker or an ICM may be electrically connected to the battery 158. The cathode pin 350 may also be referred to as a "cathode lead" or a "cathode post" or "cathode terminal" and may include an electrical conductor such as a wire, a fiber, a pin or other suitable structure.

In some embodiments, the case 310 may be a titanium or titanium alloy case. Additionally or alternatively, the case 310 may be a clamshell style case. Further additionally or alternatively, the case 310 may be formed from or otherwise include other suitable materials, such as aluminum, stainless steel, nickel alloys, or other biocompatible materials.

Although not shown in FIG. 3, an electrolyte (or electrolyte system) is included in the battery 158 to facilitate ion transport between the anodic and cathodic regions. The electrolyte system may include a polymer or a liquid electrolyte. Examples of the electrolyte system include lithium bis-trifluoromethanesulfonimide (LiTFSI) in propylene carbonate/dimethoxyethane, lithium hexafluoroarsenate (LiAsF6) in propylene carbonate/dimethoxyethane, lithium hexafluorophosphate (LiPF6) in propylene carbonate/dimethoxyethane, lithium bis(fluorosulfonyl)imide (LiFSI) in propylene carbonate/dimethoxyethane, or the like.

In some embodiments, the solvents used in the electrolyte system may be one or more of propylene carbonate (PC), dimethoxyethane (DME), ethylmethyl carbonate (EMC), dimethyl carbonate (DMC), diethyl carbonate (DEC), or the like. Optionally, other suitable solvents may be used in combination with the electrolyte salts. Additionally or alternatively, additives may be added to the electrolyte system in combination with the solvents. The additives may be one or more of diphenol carbonate (DPC), dibutyl carbonate (DBC), or the like. Additionally or alternatively, the electrolyte system may include lithium hexafluoroarsenate (LiAsF6) in propylene carbonate/dimethoxyethane, and dibutyl carbonate (DBC), or the like.

In some embodiments, the battery 158 may be based on a prismatic stacked cell design capable of 4.4 A (amperes) of current and 2200-2500 mAh of theoretical capacity. Additionally or alternatively, the battery 158 may be a prismatic cell having a volume in the range of 3 cc to 10 cc. Additionally or alternatively, the battery 158 may be configured for implementation in low to medium current applications (e.g., microamperes to milliamperes). Further additionally or alternatively, the battery 158 may be a rechargeable battery. By way of example, the battery may have structures described in U.S. Pat. No. 6,937,894, titled "Method of Recharging Battery for an Implantable Medical Device", issuing Aug. 30, 2005; U.S. Pat. No. 6,549,807, titled "Implantable Cardioverter Defibrillator Having a Rechargeable, Fast Charging Battery and Method Thereof", issuing Apr. 15, 2003; U.S. Pat. No. 10,403,903, titled "Low-Rate Battery Design", issuing Sep. 3, 2019; U.S. Pat. No. 10,263,240, titled "Sandwich Cathode Lithium Battery with High Energy Density", issuing Apr. 16, 2019; U.S. Pat. No. 10,038,220, titled "Nonaqueous electrolyte for lithium battery safety" issuing Jul. 31, 2018, all of which are expressly incorporated by reference in their entireties.

In additional or alternative embodiments, the battery 158 may include a weight ratio of the electrolyte to the active cathode material of 0.25 to 0.4.

Figure 4A:
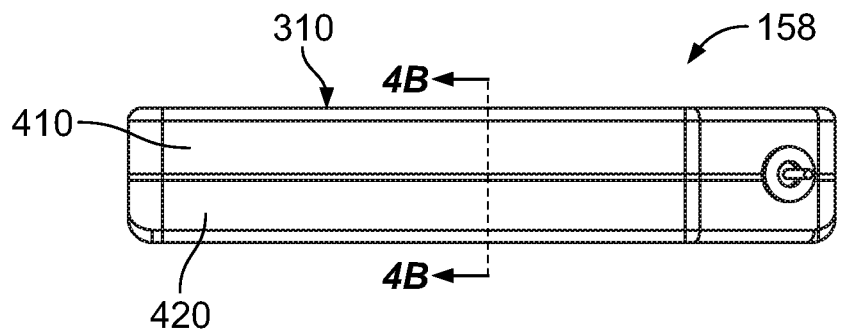
FIG. 4A illustrates an edge view of the example battery of FIG. 3 in accordance with embodiments herein.
Figure 4B:
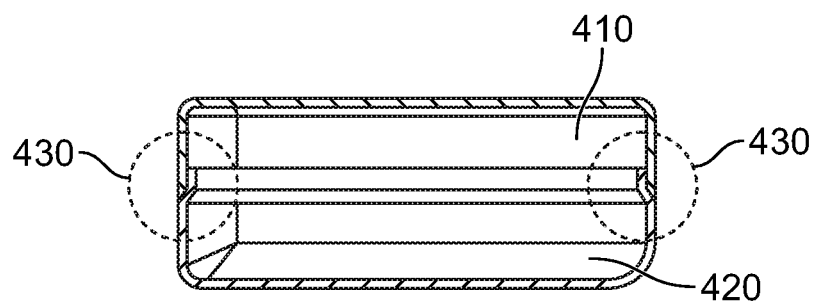
FIG. 4B illustrates a transverse cross-section taken along line 2-2' of FIG. 4A in accordance with embodiments herein.

FIG. 4A illustrates an edge view of the example battery of FIG. 3 in accordance with embodiments herein and FIG. 4B illustrates a transverse cross-section taken along line 2-2' of FIG. 4A. The battery 158 includes the feedthrough assembly 330. The case 310 may include a lid 410 and a base 420. In a closed configuration of the case 310, the lid 410 and the base 420 mate in an overlapping manner to form a hermetic seal 430 around the periphery of the case 310. The hermetic seal 430 provides a continuous and impermeable barrier between the components of the battery 158 enclosed by the case 310 and the external environment (e.g., the internal components of the IMD 100). The hermetic seal 430 also prevents the electrolyte from leaking out of the case 310 and/or eliminates infiltration of any external fluids into the battery 158.

In some embodiments, the case 310 may include a hinge (not shown) joining the lid 410 and the base 420. The hermetic seal between the lid 410 and the base 420 may be formed by joining the lid 410 and the base 420 around the periphery of the case 310 by one or more of heat-sealing, compression joints, snap-fit joints, friction-fit joints, pressure-sensitive tapes, adhesives, welding, soldering, brazing, or the like.

Figure 5A:
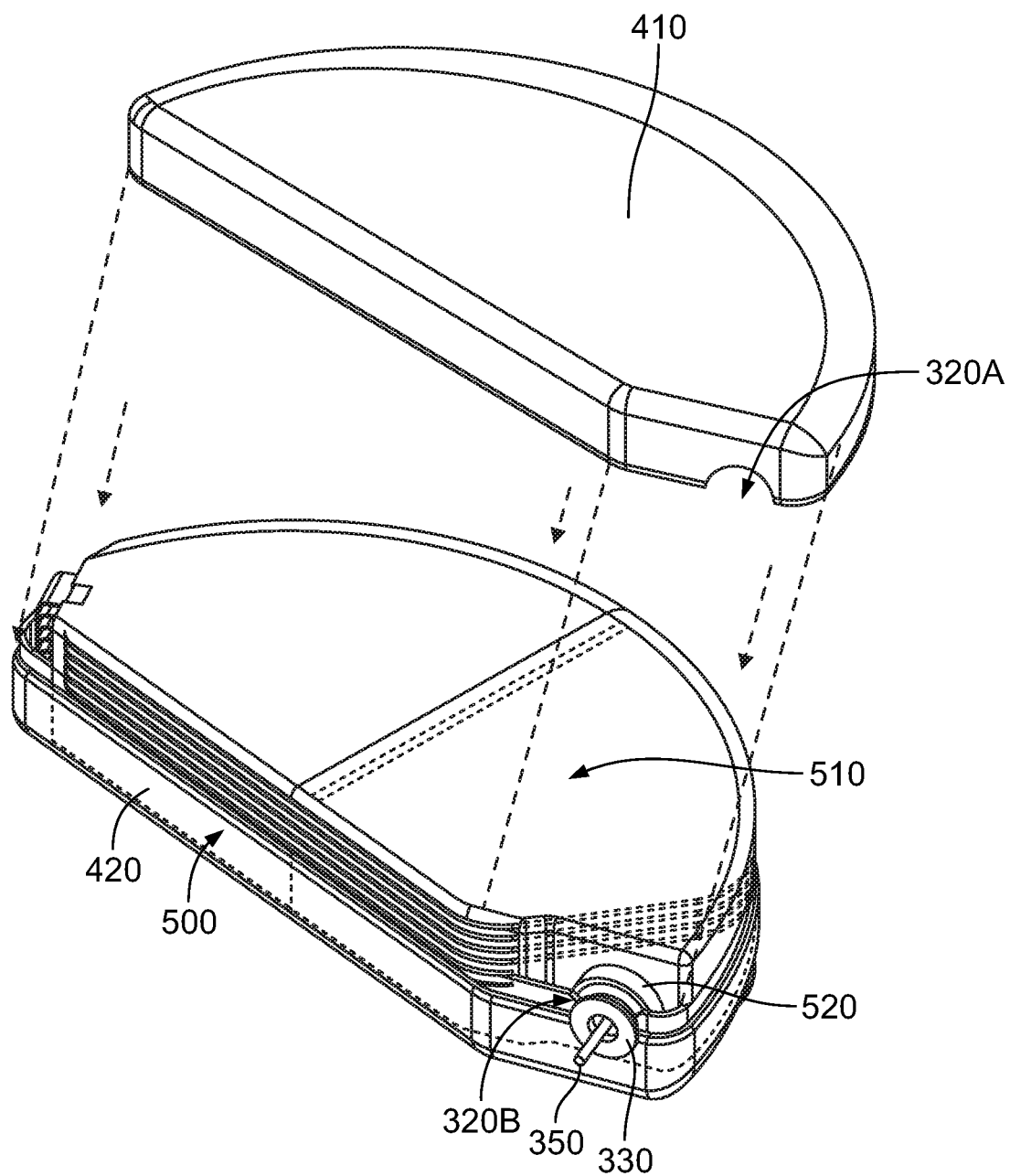
FIG. 5A illustrates a perspective view of the example battery of FIG. 3 having the lid of the case removed in accordance with embodiments herein.

FIG. 5A illustrates a perspective view of the example battery of FIG. 3 having the lid of the case removed in accordance with embodiments herein. The lid 410 includes an opening 320A which forms a first portion of the feedthrough port 320. The base 420 includes an opening 320B which forms a second portion of the feedthrough port 320. The openings 320A and 320B align to form the feedthrough port 320 when the lid 410 is jointed to the base 420. A cell stack 500 may be disposed within the case 310.

The cell stack 500 may be encased in an insulating boot 510 disposed in the case 310. The insulating boot 510 may be configured to physically and electrically insulate the cell stack 500 from the case 310. For example, insulating boot 510 may prevent short circuiting between an anode terminal 530 (shown in FIG. 5B), which may be electrically connected to case 310, and the cathode terminal or pin 350. The insulating boot 510 may include a feedthrough opening 520 aligned coaxially with the feedthrough port 320, and may be configured to receive the feedthrough assembly 330 therethrough. In some embodiments, the insulating boot 510 with the feedthrough opening 520 may be formed by vacuum forming, injection molding, press-molding, or other suitable methods including a combination of known methods. Alternatively, feedthrough opening 520 may be created after insulating boot 510 is formed. Example methods of forming feedthrough opening 520 include punching, drilling, cutting, and etching through insulating boot 510.

In additional or alternative embodiments, the insulating boot 510 may be formed from an electrically insulating material that is compatible with the electrochemical system and can be thermally or mechanically bonded to the feedthrough assembly 330. The insulating boot 510 may be formed from, for example and without limitation, vacuum formed plastic, polypropylene (PP), polyethylene (PE), polycarbonate (PC), ethylenetetrafluoroethylene (ETFE), Surlyn®, polyether ether ketone (PEEK), or the like, or mixtures of the foregoing. For example, insulating boot 510 may be formed from polyethylene (PE) and/or ethylenetetrafluoroethylene (ETFE). Additionally or alternatively, the insulating boot 510 may also be formed from the same electrically insulating material or materials used to form the anode and/or cathode separators, as will be described further below. Further additionally or alternatively, the insulating boot 510 may be a tape or any other type of insulating material and/or structure that can hold the cell stack 500 together.

Figure 5B:
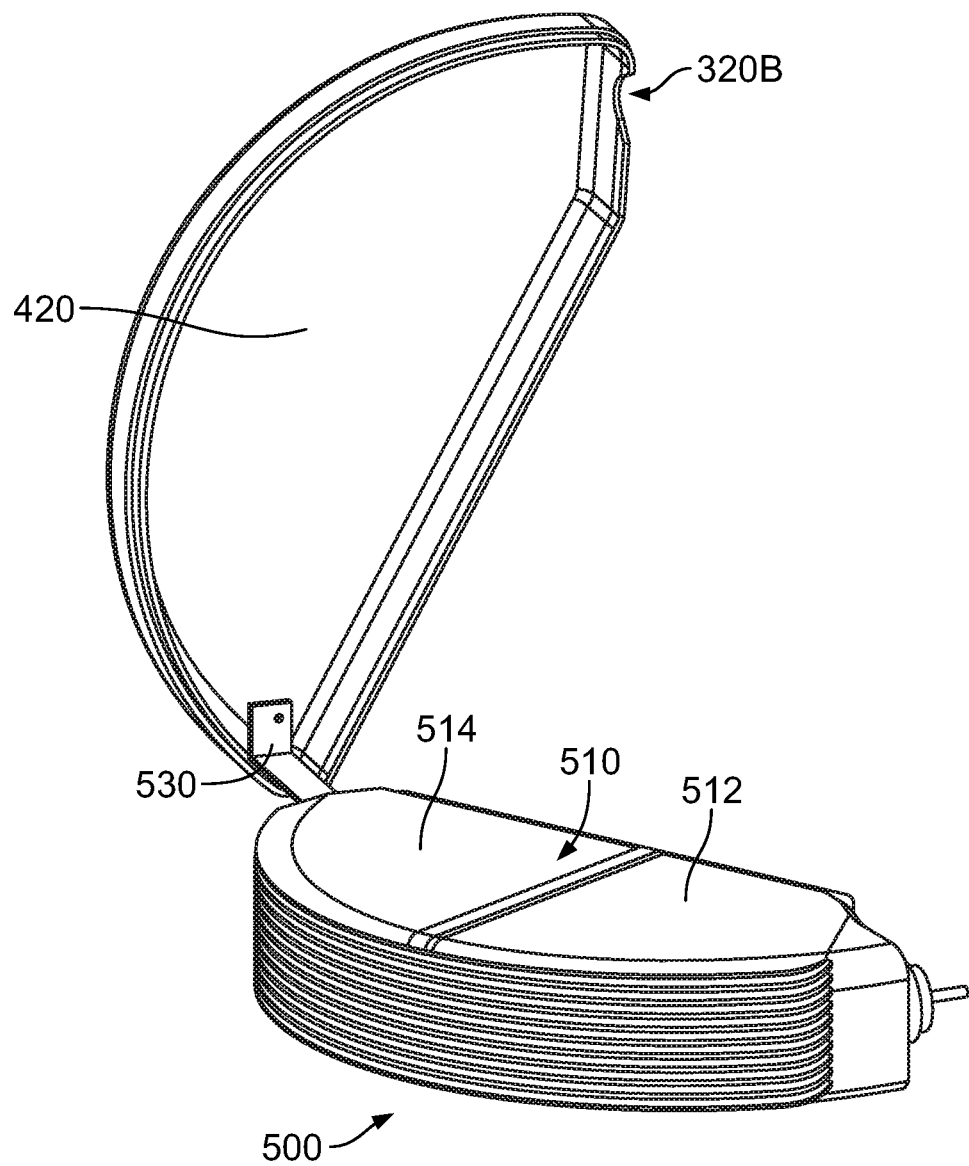
FIG. 5B illustrates a perspective view of a cell stack connected to the base of case of the example battery of FIG. 3 in accordance with embodiments herein.

FIG. 5B illustrates a perspective view of a cell stack connected to the base of case of the example battery of FIG. 3 in accordance with embodiments herein. The insulating boot 510 may surround the cell stack 500. The cell stack 500, discussed further below, may include at least an anode having an anode tab 530. The anode tab 530 electrically connects the anode (or anodes or anode assembly) in the cell stack 500 to the base 420. The base 420 may form the negative or anode terminal 340 of the battery 158. The anode tab 530 may be an electrical conductor formed from a suitable metal (e.g., graphite carbon, lithium titanate, or the like). The anode tab 530 may be joined (e.g., spot welded) to an inner surface of the base 420. Additionally or alternatively, the anode tab 530 may be directly connected to the lid 410 of the case 310.

Figure 5C:
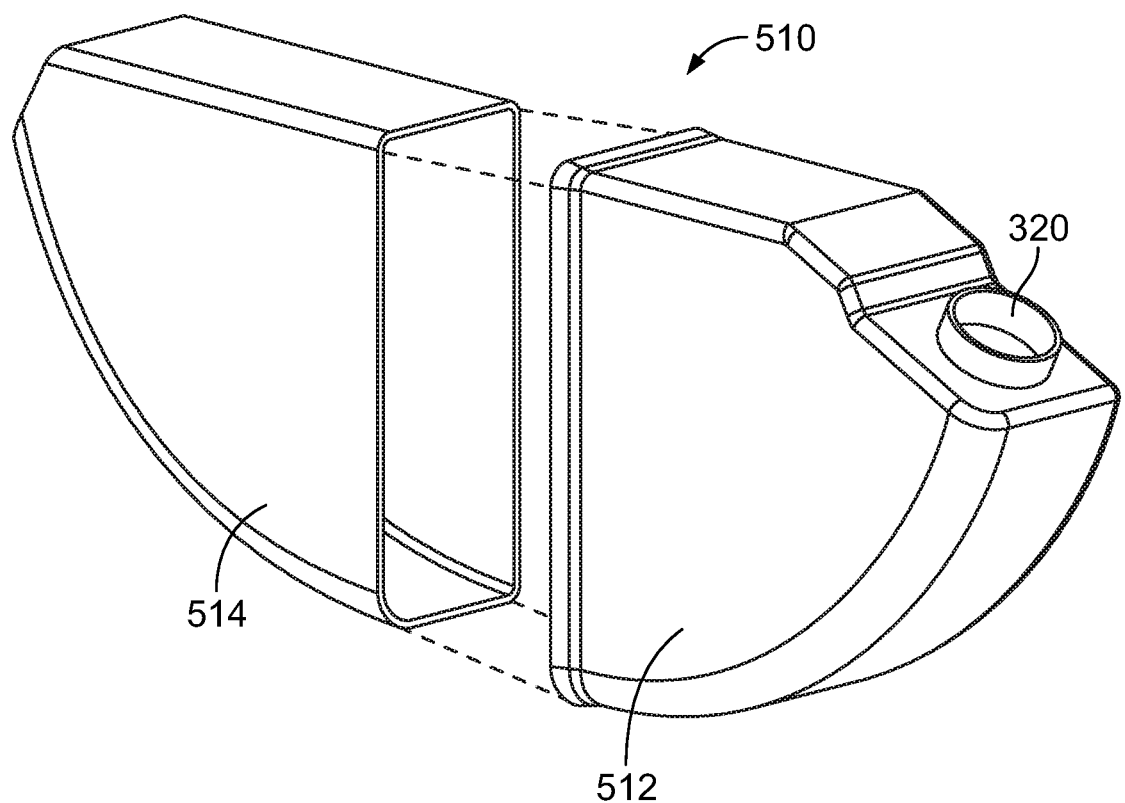
FIG. 5C illustrates a perspective view of an example insulating boot in accordance with embodiments herein.

FIG. 5C illustrates a perspective view of an example insulating boot in accordance with embodiments herein. The insulating boot 510 may include a front portion 512 and a tail portion 514. The "front" portion includes the portion (e.g., approximately half) of the insulating boot 510 that includes the feedthrough opening 320. The "tail" portion refers to the remaining portion of the insulating boot 510. Similarly, the portion of the battery 158 where the feedthrough port 320 is disposed may be referred to as the "front" end or "header" of the battery 158. The remaining portion of the battery 158 may be referred to as the "tail" end of the battery 158. The front portion 512 and tail portion 514 of the insulating boot 510 may be overlapped and sealed to encase and insulate the cell stack 500 from the case 310. Sealing may include one or more of thermal bonding, mechanical bonding, adhesive bonding, or the like.

In additional or alternative embodiments, the insulating boot 510 may be split along a perpendicular axis to form a top half and a bottom half, rather than a front portion and a tail portion. Additionally or alternatively, the front portion 512 and/or the tail portion 514, may be further split along a perpendicular axis to form a top half and a bottom half. The top halves and the bottom halves may be bonded together by one or more of thermal bonding, mechanical bonding, adhesive bonding, or the like.

Figure 6A:
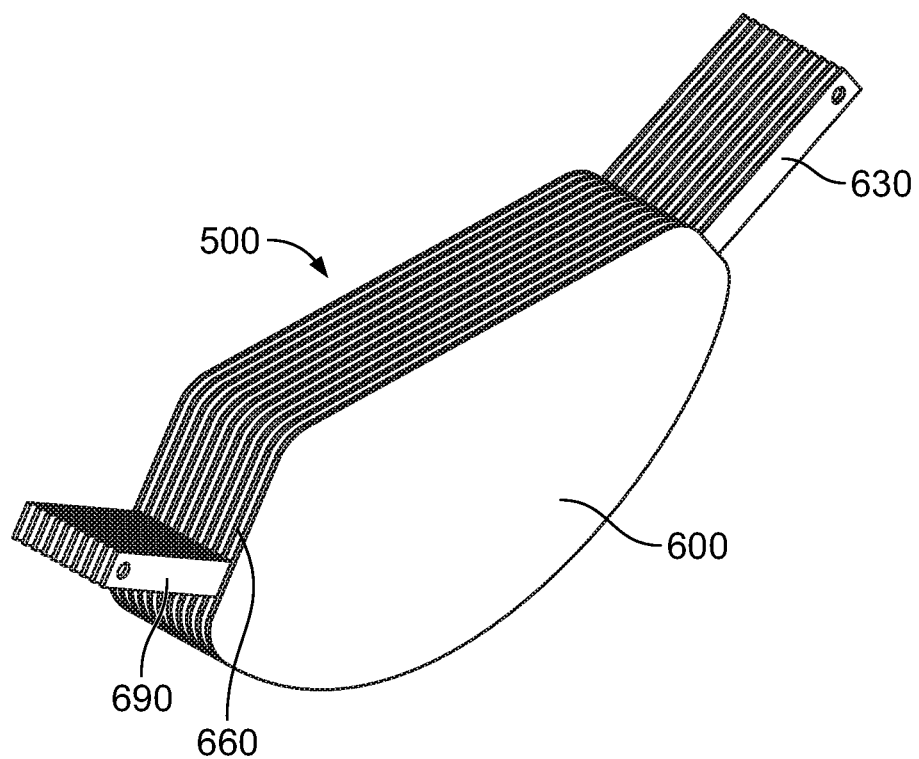
FIG. 6A illustrates a perspective view of an example cell stack in accordance with embodiments herein.
Figure 6B:
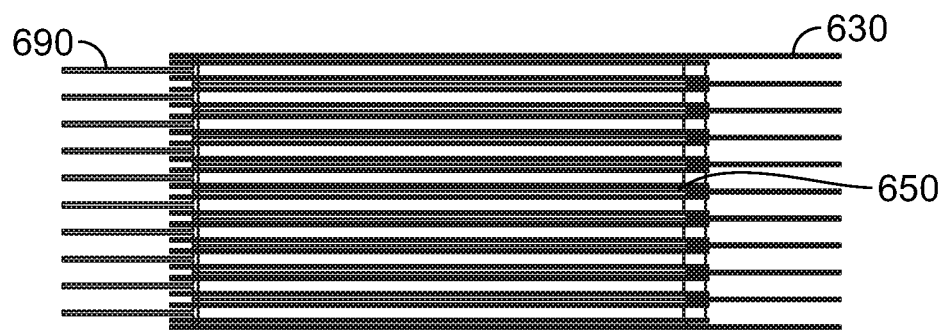
FIG. 6B illustrates an edge view of the cell stack of FIG. 6A in accordance with embodiments herein.

FIG. 6A illustrates a perspective view of an example cell stack and FIG. 6B illustrates an edge view of the cell stack of FIG. 6A in accordance with embodiments herein. The cell stack 500 may include anodes 600 and one or more cathodes 660 stacked in an alternating manner. A separator 650 may electrically insulate each of the anodes 600 from the cathodes 660. The anodes 600 (or anode assembly) may include an anode current collector tab 630, and the cathode(s) 660 (or cathode assembly) may include a cathode current collector tab 690. In some examples, the separator 650 may include a micro-porous or a nano-porous material. The separator 650 may have an average pore size in the range of 0.02 µm to 0.5 µm. Additionally or alternatively, the average pore size of the separator 650 may be 0.05 µm.

Figure 7:
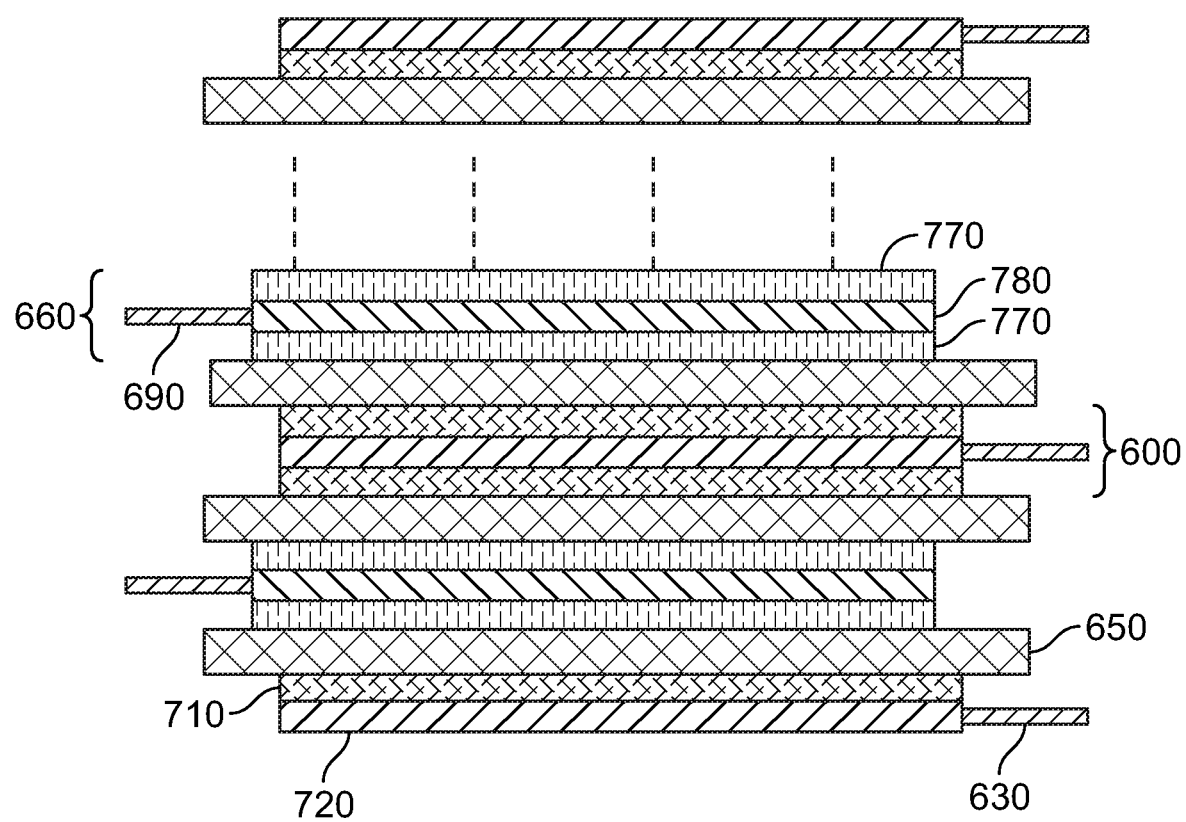
FIG. 7 illustrates an example anode/cathode alignment in a cell stack in accordance with embodiments herein.

FIG. 7 illustrates an example anode/cathode alignment in a cell stack in accordance with embodiments herein. Each anode 600 may include a pair of anode foils 710 pressed together against the opposite sides of an anode current collector 720 having the anode current collector tab 630. The anode foils 710 may be positioned in electrical contact with the anode current collector 720. The anode current collector tabs 730 may be gathered and joined (e.g., welded) together to the anode tab 530. The anode tab 530 may be joined (e.g., spot-welded) to a portion (e.g., the base 420) of the case 310. Alternatively, the anode current collector tabs 730 may be gathered and joined (e.g., welded) together to form the anode tab 530. The anode foils 710 may include lithium metal or the like. The anode current collector 720 may include a plate that may be formed from nickel, stainless steel, or the like. The plate may have a thickness of 0.005 inches or less. The plate of the anode current collector 720 may be solid, mesh, or the like.

Each cathode 660 may include a pair of cathode blanks 770 pressed together against the opposite sides of a cathode current collector 780 having the cathode current collector tab 690. The cathode blanks 770 may be positioned in electrical contact with the cathode current collector 780. The cathode current collector 780 may be formed from a common material as the inner conductor (FIGS. 12A and 12B) of the feedthrough assembly 330. The cathode current collector tabs 690 may be gathered and joined (e.g., welded) together to the cathode tab. The cathode tab may be electrically connected to the cathode pin 350 of the feedthrough assembly 330. Alternatively, the cathode current collector tabs 690 may be gathered and joined (e.g., welded) together to form the cathode tab.

Figure 8:
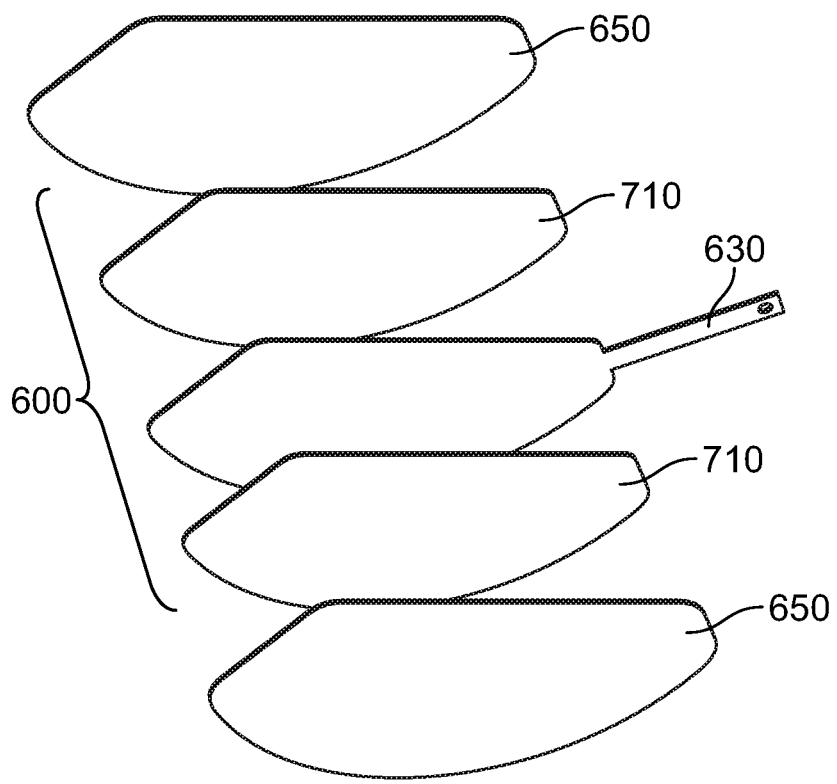
FIG. 8 illustrates an exploded view of an example anode in accordance with embodiments herein.

FIG. 8 illustrates an exploded view of an example anode in accordance with embodiments herein. The anodes 600 may be encapsulated by the separators 650. The separators 650 electrically insulate the anode 600 from the cathodic surfaces of the cell stack 500. For example, the anode 600 may be encapsulated by sealing the anode foils 710 and the anode current collector 720 in a shut-down separator bag (or sleeve) formed from the same material that forms the separators 650. The separator 650 may include a permeable membrane that electrically isolates the anode 600 from the cathode 660, while still allowing the transport of ions (e.g., Li+ ions) therethrough to facilitate passage of electric current in the battery 158. The separator 650 (or the shut-down separator bag) may be formed from one or more of paper, cotton, polyethylene, polypropylene, polytetrafluoroethylene, ceramics, rubber, or the like, or mixtures thereof.

Figure 9:
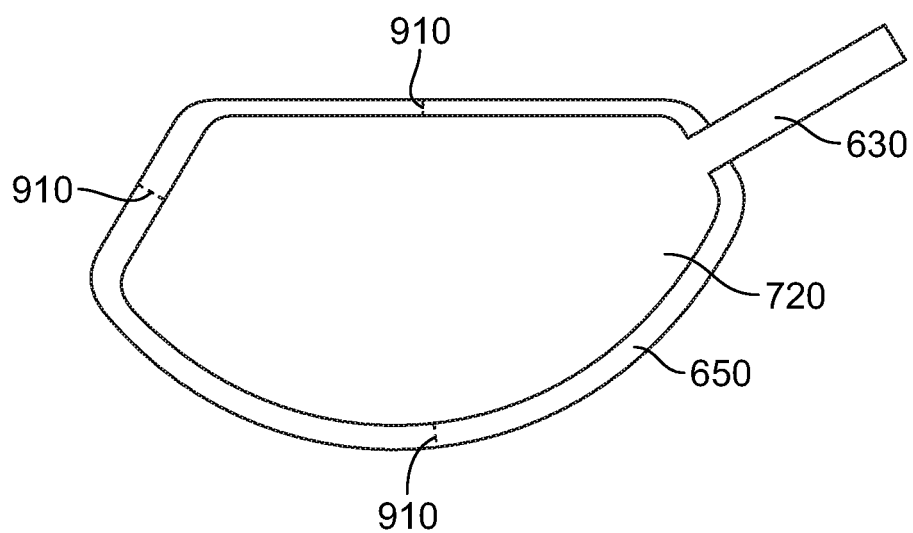
FIG. 9 illustrates a plan view of the example anode of FIG. 9 in accordance with embodiments herein.

FIG. 9 illustrates a plan view of the example anode of FIG. 9 in accordance with embodiments herein. A periphery of the separator 650 may protrude beyond a periphery of the anode current collector 720 and the anode foils 710 (not shown). The anode foils 710 may be equally sized with the anode current collector 720. The protrusion of the separator 650 outside the periphery of the anode current collector 720 may ensure electrical isolation between the anode 600 and the cathodic surfaces.

In some embodiments, the separator 650 extends outward beyond the entirety of the periphery of the anode current collector 720 and the anode foils 710. The protrusion length 910, measured in a direction perpendicular to the peripheral edges, may be at least two times the thickness of the anode. For example, the protrusion length may be between about three times and about five times the anode thickness. The protrusion length 910 may be uniform around the periphery. Additionally or alternatively, the protrusion length 910 may be non-uniform and/or uniformly vary around the periphery.

Figure 10:
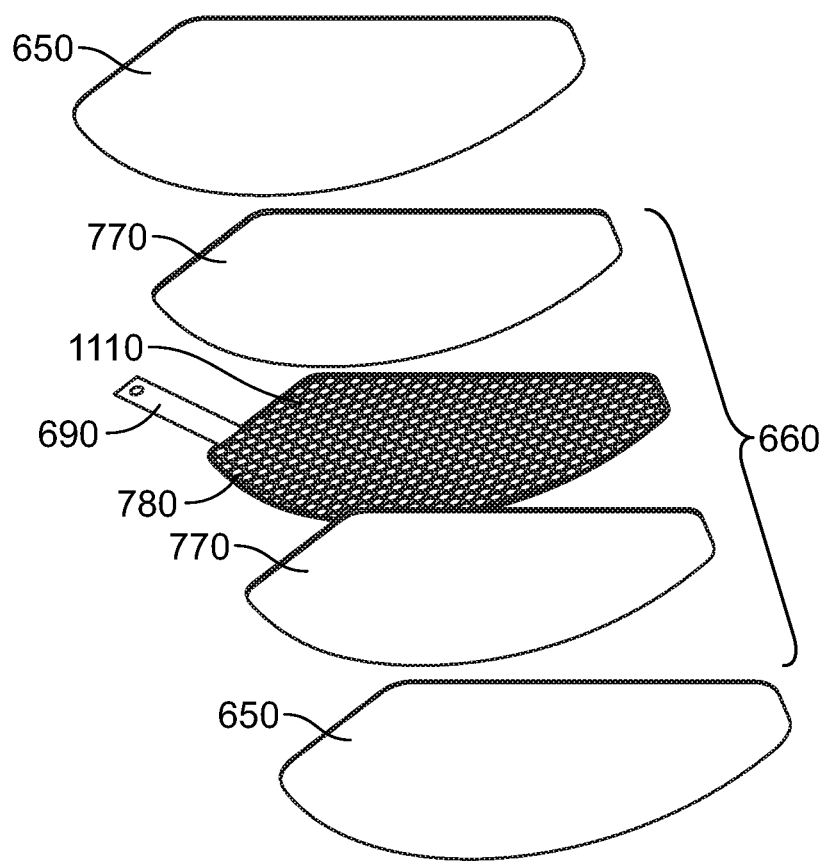
FIG. 10 illustrates an exploded view of an example cathode in accordance with embodiments herein.

FIG. 10 illustrates an exploded view of an example cathode in accordance with embodiments herein. The cathode 660 may include a pair of cathode blank cathode blanks 770 pressed together against opposite sides of the cathode current collector 780 having the cathode current collector tab 690. The cathode blanks 770 may be positioned in electrical contact with the cathode current collector 780. The cathode current collector 780 may include a mesh structure 1010, as discussed further below. Each of the cathode blanks 770 includes an active cathode material. For example, the active cathode material may include a mixture of an oxide (e.g., silver vanadium oxide (SVO), carbon monofluoride (CFx), cobalt oxide, lithium manganese oxide, nickel-manganese-cobalt oxide, lithium phosphate oxide, nickel cobalt aluminum oxide, or the like), a conductor (e.g., carbon, carbon black, or the like) and a binder. Additionally or alternatively, the active cathode material may include a mixture of silver vanadium oxide and carbon monofluoride (CFx). In one example, the active cathode material may include a mixture containing 94% SVO, 2% carbon, 1% graphite, and 3% poly-tetrafluoroethylene (PTFE) by weight.

In some embodiments, the cathode 660 may be encapsulated by the separators 650. The separators 650 electrically insulate the cathode 660 from the anodic surfaces of the cell stack 500. For example, the cathode 660 may be encapsulated by sealing the cathode blanks 770 and the cathode current collector 780 in a shut-down separator bag (or sleeve) formed from the same material that forms the separators 650.

In additional or alternative embodiments, the cathode blanks 770 and the cathode current collector 780 may be laminated together. For example, the cathode blanks 770 and the cathode current collector 780 may be laminated using pressure in the range of about 5 kilopounds per square inch (ksi) to about 100 ksi. Additionally or alternatively, the pressure range may be 30-60 ksi. Further additionally or alternatively, the pressure may be 40 ksi with an active loading range of 71 mg·cm2 to 73 mg·cm2. The cathode compaction force may directly impact the completed cell performance. Compaction forces greater than 52 ksi may result in a decrease in power output of the cells when multiple pulses are performed. Compaction forces less than 47 ksi may result in an increase in power output of the cells when multiple pulses are performed. The lower compaction force may create a less dense cathode and may allow lithium ions to move more freely into the cathode. Furthermore, the lower compaction force may reduce the polarization of the cells during multi-pulse performance, resulting in the cells depolarizing faster.

Figure 11:
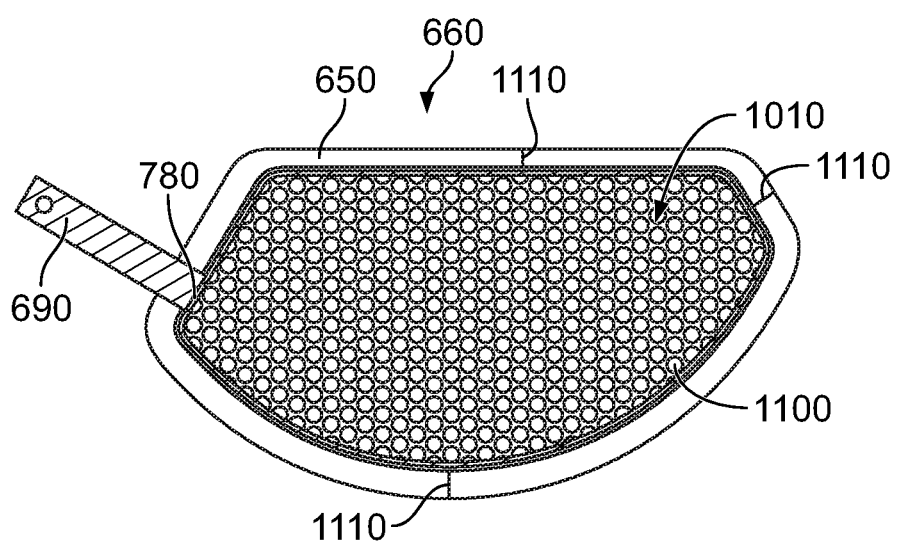
FIG. 11 illustrates a plan view of the example cathode of FIG. 10 in accordance with embodiments herein.

FIG. 11 illustrates a plan view of the example cathode of FIG. 10 in accordance with embodiments herein. The cathode current collector 780 is stacked on top of a cathode blank 870 and a separator 650. The cathode current collector 780 may be formed from a mesh structure 1010. Active cathode material layers may be placed on either side of the cathode current collector 780. The active cathode material layers may be bonded to the mesh structure 1010 and/or to each other through the openings 1100 in the mesh structure 1010. The openings 1100 may be repeated uniformly along the entire surface of the cathode current collector 780 to form a repeating pattern. The mesh structure 1010 may be characterized by an opening percentage. The opening percentage is a percentage of the surface area of the mesh structure 1010 that is represented by open space as compared to the same surface area of a solid material. A higher opening percentage of the mesh structure 1010 may reduce the weight and/or volume of the cathode current collector 780. The reduced weight and/or volume of the cathode current collector 780 may increase the total cell packing efficiency of the battery 158.

In some embodiments, the opening percentage of the mesh structure 1010 may be about 20% to about 98%. For example, the mesh structure 1010 may have an opening percentage of 60% to 80%.

In additional or alternative embodiments, the openings 1100 may be one or more of rectangles, squares, pentagons, hexagons, octagons, circles, ovals, or the like, or combinations thereof. For example, the openings 1100 may be hexagonal openings. An advantage of hexagonal openings may be that they do not include any acute angles. The lack of acute angles may facilitate bonding of the active cathode material on either side of the mesh structure 1010 through the openings 1100 and may increase the mechanical integrity of the cathode 660.

In additional or alternative embodiments, the cathode current collector 780 and/or the mesh structure 1010 may be one or more of machined, cast, stamped, forged, or the like. the cathode current collector 780 and/or the mesh structure 1010 may be formed from a metal such as aluminum, stainless steel, or titanium, or the like. Additionally or alternatively, a conductive coating (e.g., a carbon coating) may be applied to the surface of the mesh structure 1010 to increase binding strength and/or electrical conductivity. The cathode current collector 780 may have a total thickness in the range of about 0.001 inches to about 0.005 inches. The cathode current collector 780 may include one or more aspects described in U.S. patent application Ser. No. 15/649,270, entitled "Electrode Current Collector Design in A Battery" and filed on Jul. 13, 2017, the disclosure of which is hereby incorporated herein by reference in its entirety.

Hermetic Feedthrough Assembly

Figure 12A:
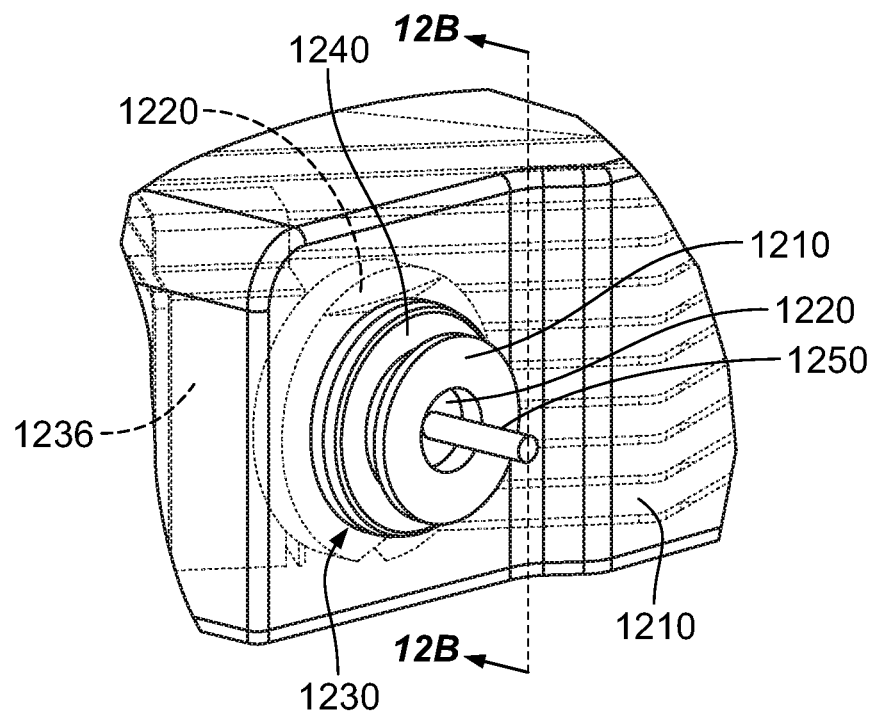
FIG. 12A illustrates a partial perspective view of an example feedthrough assembly in accordance with embodiments herein.
Figure 12B:
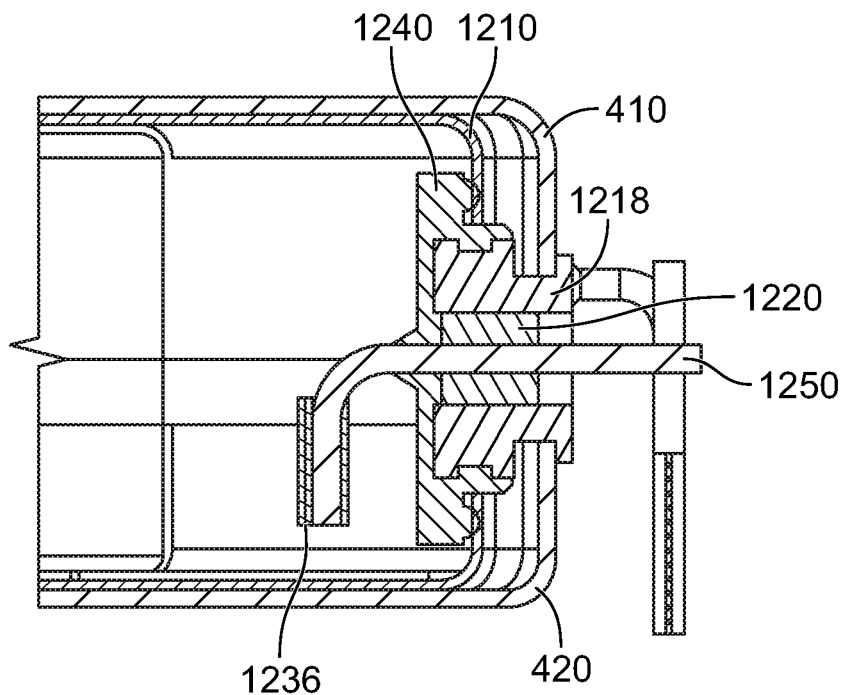
FIG. 12B illustrates a cross-sectional view of the example feedthrough assembly of FIG. 12A taken along line 12-12' in accordance with embodiments herein.

FIG. 12A illustrates a partial perspective view of an example feedthrough assembly and FIG. 12B illustrates a cross-sectional view of the example feedthrough assembly of FIG. 12A taken along line 12-12' of FIG. 12A in accordance with embodiments herein. A case 1210 includes a feedthrough assembly 1230 disposed in a feedthrough port 1220. The case 1210 may represent a housing 101 of the IMD 100 and/or a case 310 of the battery 158. In one example, the case 1210 may be the case 310 and the feedthrough assembly 1230 may be the feedthrough assembly 330 of the battery 158. Additionally or alternatively, the base 420 and the lid 410 of the case 310 of the battery 158 may be hermetically joined to each other and to the metal ferrule 1210 at the feedthrough port 320. The feedthrough assembly 1230 may be connected to a cathode tab 1236 of the cell stack 500 of the battery 158. The feedthrough assembly 1230 may be a GTMS feedthrough. For example, the inner conductor 1250 may be a cathode pin electrically connected to the cathode tab 1236 inside of case 1210. Alternatively, the inner conductor 1250 may be an anode pin connected to an anode tab inside of the case 1210. The other end of the inner conductor 1250 may extend outward from the case 1210 for connection to an external load on the battery 158 (e.g., IMD circuitry, external electronics, or the like).

The feedthrough assembly 1230 includes a ferrule 1218 defining a lumen. An inner conductor 1250 is disposed within the lumen of the ferrule 1218. An insulating core 1220 is disposed within the lumen of the ferrule 1218 and separates the inner conductor 1250 from the ferrule 1218 and/or the case 1210. The inner conductor 1250 is formed from a material having a first composition and a first CTE. The insulating core 1220 is formed from a material having a second composition and a second CTE. The first CTE of the inner conductor 1250 is equal to or greater than the second CTE of the insulating core 1220. The insulating core 1220 may be formed from a low silica or silica-free insulating glass (e.g., Ta-23, CABAL-12, or the like). Additionally, the insulating core 1220 does not form a compression seal with the inner conductor 1250 due, at least in part, to the first CTE of the inner conductor 1250 being equal to or greater than the second CTE of the insulating core 1220. For example, the coefficient of thermal expansion (CTE) of the inner conductor 1250 formed from titanium (e.g., having a CTE of about 9×10–6/° C.) is greater than the CTE of an insulating core 1220 formed from CABAL-12 (e.g., having a CTE of 6×10-6/° C.).

The inner conductor 1250 is formed from a material having a melting point at or below 4500° F. Additionally or alternatively, the inner conductor 1250 is formed from a material having a melting point that is within an acceptable range of a melting point of the material forming the insulating core 1220 to avoid undue damage to the insulating core 1220 when electrically coupling one or both ends of the inner conductor 1250 to corresponding electronics (e.g., IMD circuitry or external electronics), the cell stack 500, or the like. By way of example, the inner conductor 1250 may be formed from a material having a melting point of between 2000° F. and 4500° F., or more preferably a melting point between 2000° F. and 4000° F., and even more preferably between 2800° F. and 3200° F. Nonlimiting examples of materials that may be utilized to form the inner conductor 1250 include titanium (e.g., grade 1 titanium, grade 2 titanium, or the like), niobium, or the like The inner conductor 1250 is formed from a material that exhibits a certain level of electrical conductivity sufficient to carry low-level current that is output by a battery of the type that is well-suited to power implantable medical devices.

The first composition of the inner conductor 1250 and the second composition of the insulating core 1220 are molecularly bonded with one another to form a hermetic seal between the inner conductor 1250 and the insulating core 1220. The first composition of the inner conductor 1250 may include an oxide based composition on the surface of the inner conductor 1250 and the second composition of the insulating core 1220 may also include an oxide based composition. The molecular bond may represent a chemical bond between the oxide based compositions of the first and second compositions to form the hermetic seal. Additionally or alternatively, the inner conductor 1250 may include an oxidized form of the first composition disposed on the outer surfaces thereof and the oxidized form of the first composition may be molecularly bonded with the oxide based second composition of the insulating core 1220 to form the hermetic seal between the inner conductor 1250 and the insulating core. Further additionally or alternatively, the molecular bonding is facilitated by good wettability of the insulating core 1220 (e.g., CABAL-12, TA-23, or the like) by an inner conductor 1250 formed from titanium during a GTMS production process (e.g., including heating the feedthrough assembly to melt and flow the insulating core and cooling the feedthrough assembly to re-solidify the insulating core).

In additional embodiments, the inner conductor 1250 and the ferrule 1218 may be made of a common material. Additionally or alternatively, the ferrule 1218 may be formed from a material having a third CTE that is also greater than the second CTE of the insulating core 1220 and, optionally, may be the same as the first CTE of the of the inner conductor 1250. For example, the coefficient of thermal expansion (CTE) of the inner conductor 1250 and the ferrule 1218, both formed from titanium (e.g., having a CTE of about 9×10–6/° C.), are greater than the CTE of an insulating core 1220 formed from CABAL-12 (e.g., having a CTE of 6×10–6/° C.). Additionally or alternatively, the cathode current collector 780 and/or the mesh structure 1010 may be formed from a common material as the inner conductor 1250 and/or the ferrule 1218.

Optionally, the ferrule 1218 may be at least partially surrounded by feedthrough insulation 1240. The feedthrough insulation 1240 includes an insulating material. Additionally or alternatively, the feedthrough insulation 1240 may be joined to the ferrule 1210 by one or more of an adhesive, a thermal bond, a compression bond, or the like. For example, a thermal bond between the feedthrough insulation 1240 and the ferrule 1210 may be formed by one or more of laser welding, resistive welding, friction welding, radio-frequency (RF) welding, or the like. The feedthrough insulation 1240 may include an electrically insulating material including one or more of polypropylene (PP), polyethylene (PE), polycarbonate (PC), ethylenetetrafluoroethylene (ETFE), Surlyn®, polyether ether ketone (PEEK), silicones, polyurethane (PU), or the like. Additionally or alternatively, the feedthrough opening 520 in the front portion 512 of the insulating boot 510 and the overmolded feedthrough insulation 1240 of the feedthrough assembly 1230 may be bonded together to form a continuous liquid-tight seal. The feedthrough insulation 1240 and insulating boot 510 may be one or more of adhesively bonded, thermally bonded (e.g., via laser welding, resistive welding, friction welding, RF welding, or the like), compression-sealed through mechanical interference, or the like. The liquid-tight seal may be configured to prevent lithium cluster or lithium dendrite infiltration between the cathode pin 1250 and adjacent anodic structures, such as the metal ferrule 1218, adjacent portions of the anodes, and adjacent areas of case 1210.

Figure 13A:
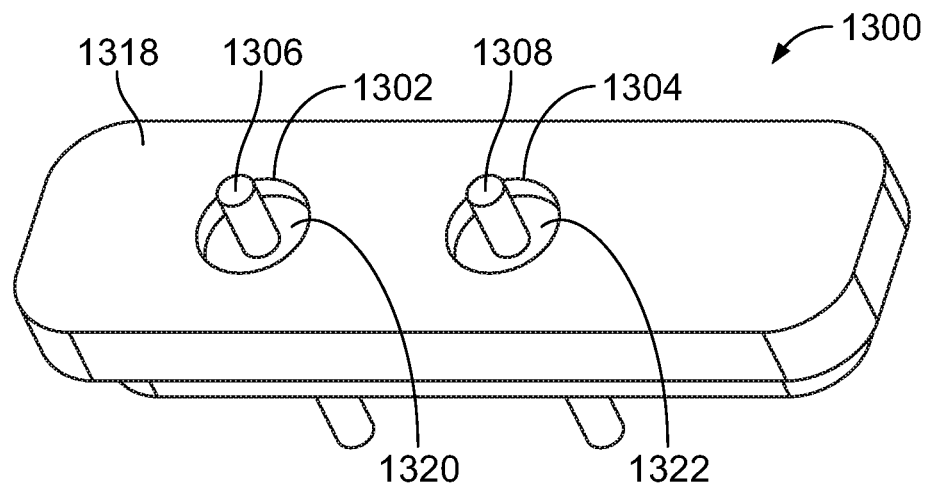
FIG. 13A illustrates a perspective view of another example feedthrough assembly in accordance with embodiments herein.
Figure 13B:
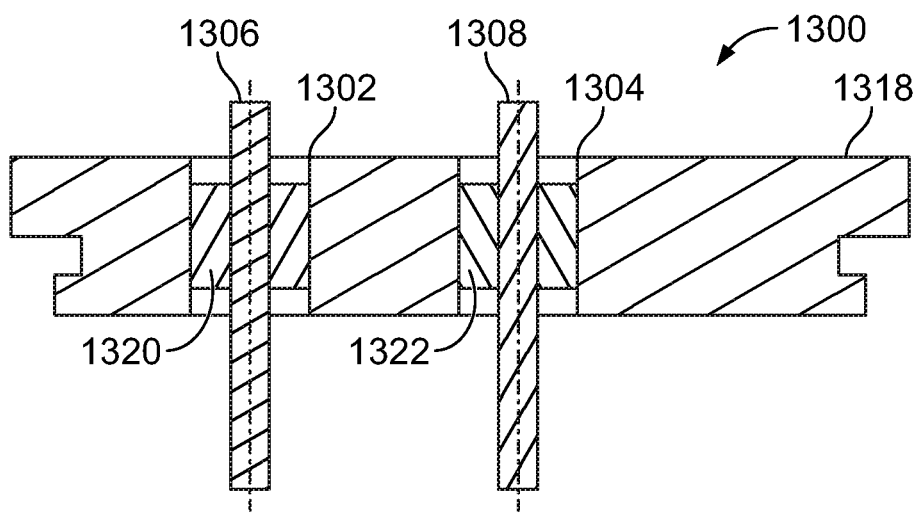
FIG. 13B illustrates a cross-sectional view of the example feedthrough assembly of FIG. 13A taken along line 13-13' in accordance with embodiments herein.

FIG. 13A illustrates a perspective view of another example feedthrough assembly FIG. 13B illustrates a cross-sectional view of the example feedthrough assembly of FIG. 13A taken along line 13-13' in accordance with embodiments herein. The feedthrough assembly 1300 is configured to be disposed in a feedthrough port of a case. The case may represent a housing 101 of the IMD 100 and/or a case of the battery 158. The feedthrough assembly 1300 is similar to the feedthrough assembly 1230 described in FIGS. 12A and 12B, except for the differences discussed herein. The feedthrough assembly 1300 includes a ferrule 1318 that defines at least two lumens 1302, 1304. The feedthrough assembly 1300 includes an inner conductor 1306, 1308 disposed in each one of the lumens 1302, 1304. An insulating core 1320, 1322 is disposed within each lumen 1302, 1304 of the ferrule 1218 and separates the inner conductors 1306, 1308 from the ferrule 1318 and/or the case (not shown).

Figure 14:
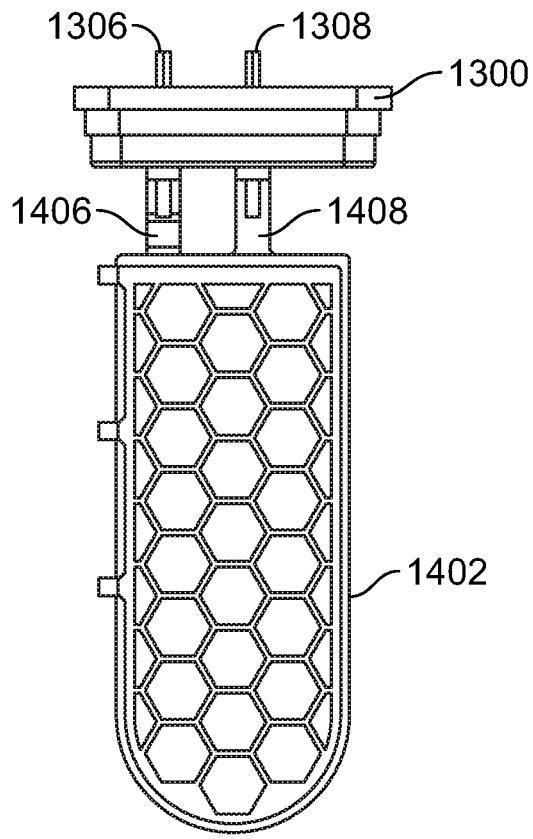
FIG. 14 illustrates an example feedthrough assembly coupled to an example cell stack of a battery in accordance with embodiments herein.

FIG. 14 illustrates the example feedthrough assembly of FIG. 13A coupled to an example cell stack of a battery in accordance with embodiments herein. The feedthrough assembly 1300 includes the inner conductors 1306, 1308 joined, respectively, to conductors 1406, 1408. One of the conductors 1406, 1408 may be part of a cathode assembly of the cell stack 1402 and the remaining one of the conductors 1406, 1408 may be part of an anode assembly of the cell stack 1402. The inner conductors 1306, 1308 may be joined to the respective one of the conductors 1406, 1408 via welding (e.g., spot welding, resistance welding, or the like).

Figure 15:
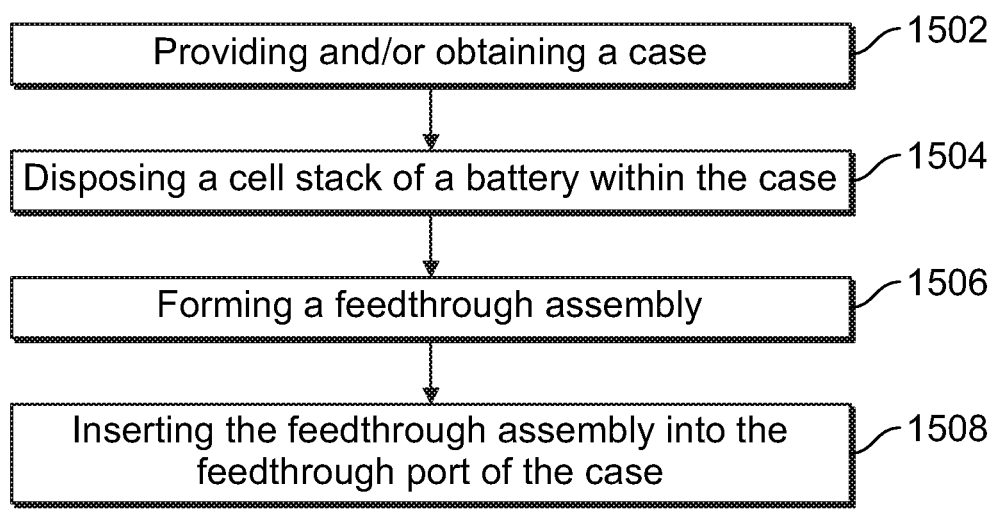
FIG. 15 illustrates a process for forming a battery feedthrough in accordance with embodiments herein.

FIG. 15 illustrates a process for forming a device including a hermetic feedthrough assembly carried out in accordance with embodiments herein, such as in accordance with one or more of FIGS. 1-14. Although the operations of FIG. 15 are described in at least a partially serial manner, it is recognized that at least a portion of the operations may be performed in parallel.

At 1502, a case 330, 1230, 1300 is provided or obtained. The case 330, 1230, 1300 may be a titanium or titanium alloy case. The case 330, 1230, 1300 may include a lid 410 and a base 420. The case 330, 1230, 1300 may be a clamshell style case, such that the lid 410 and base 420 are hinged. The case 330, 1230, 1300 includes a feedthrough port 320 provided therein. For example, the feedthrough port 320 may be provided in one or more of the lid 410 and base 420.

At 1504, a cell stack 500, 1402 is disposed within the case 310. The cell stack 500, 1402 includes an anode 600 (or anode assembly), a cathode 660 (or cathode assembly), and one or more separator layers 650 electrically insulating the anode 600 from the cathode 660.

At 1506, a feedthrough assembly 330, 1230, 1300 is formed. Forming a feedthrough assembly includes disposing an inner conductor 350, 1250, 1306, 1308 within the lumen of the ferrule 1218, 1318 and disposing an insulating core 1220, 1320, 1322 within the lumen of the ferrule that separates the inner conductor from the ferrule. The inner conductor 350, 1250, 1306, 1308 is formed from a material having a first composition and a first CTE. The insulating core 1220, 1320, 1322 is formed from a material having a second composition and a second CTE. The first CTE of the inner conductor 350, 1250, 1306, 1308 is equal to or greater than the second CTE of the insulating core 1220, 1320, 1322. The insulating core 1220, 1320, 1322 may be formed from a low silica or silica-free insulating glass (e.g., Ta-23, CABAL-12, or the like). Additionally, the insulating core 1220, 1320, 1322 does not form a compression seal with the inner conductor 350, 1250, 1306, 1308 due, at least in part, to the first CTE of the inner conductor 350, 1250, 1306, 1308 being equal to or greater than the second CTE of the insulating core 1220, 1320, 1322. For example, the coefficient of thermal expansion (CTE) of the inner conductor 350, 1250, 1306, 1308 formed from titanium (e.g., having a CTE of about $9 \times 10{-}6/^\circ$ C.) is greater than the CTE of an insulating core 1220, 1320, 1322 formed from CABAL-12 (e.g., having a CTE of $6 \times 10{-}6/^\circ$ C.).

The first composition of the inner conductor 350, 1250, 1306, 1308 and the second composition of the insulating core 1220, 1320, 1322 are molecularly bonded with one another in a GTMS process to form a hermetic seal between the inner conductor 350, 1250, 1306, 1308 and the insulating core 1220, 1320, 1322. The GTMS process includes heating the assembled components of the feedthrough assembly 330, 1230, 1300 to a temperature sufficient to cause the insulating core 1220, 1320, 1322 to melt, flow, and contact the surfaces of the lumen of the ferrule 1218, 1318 and the portions of the inner conductor 350, 1250, 1306, 1308 disposed within the lumen. The first composition of the inner conductor 350, 1250, 1306, 1308 may include an oxide based composition and the second composition of the insulating core 1220, 1320, 1322 may also include an oxide based composition. The first composition of the inner conductor 350, 1250, 1306, 1308 may have a melting point at or below 4500° F. Additionally or alternatively, the inner conductor 350, 1250, 1306, 1308 may be formed from at least one of titanium, niobium, or the like. Based on heating and flowing the insulating core 1220, 1320, 1322, a molecular bond may be formed (e.g., upon formation of a reaction layer) between at least the insulating core insulating core 1220, 1320, 1322 and the portions of the inner conductor 350, 1250, 1306, 1308 disposed within the lumen. Optionally, based on heating and flowing the insulating core 1220, 1320, 1322, a molecular bond may be formed (e.g., upon formation of a reaction layer) between the insulating core 1220, 1320, 1322 and the lumen of the ferrule 1218, 1318. The molecular bond may represent a chemical bond between the oxide based compositions of the first and second compositions to form the hermetic seal. Additionally or alternatively, the inner conductor 350, 1250, 1306, 1308 may include an oxidized form of the first composition disposed on the outer surfaces thereof and the oxidized form of the first composition may be molecularly bonded with the oxide based second composition of the insulating core 1220, 1320, 1322 to form the hermetic seal between the inner conductor 350, 1250, 1306, 1308 and the insulating core. Further additionally or alternatively, the molecular bonding may be facilitated by good wettability of the insulating core 1220, 1320, 1322 (e.g., CABAL-12, TA-23, or the like) by an inner conductor 350, 1250, 1306, 1308 formed from titanium during the GTMS production process (e.g., including heating the feedthrough assembly to melt and flow the insulating core and cooling the feedthrough assembly to re-solidify the insulating core).

At 1508, the feedthrough assembly 330, 1230, 1300 is inserted into the feedthrough port 320 of the case 310. The feedthrough assembly 330, 1230, 1300 may be inserted into the case 330, 1230, 1300 before or after the feedthrough assembly 330, 1230, 1300 is assembled and/or formed in accordance with operation 1506.

At 1510, the lid 410 and base 420 are joined to form the case 310. The joining may include hermetically sealing the lid 410 and base 420 with one another. For example, hermetically sealing the lid 410 and base 420 may include joining (e.g., welding) the lid 410 and base 420 with one another at a peripheral and/or overlapping region when the lid 410 and base 420 are joined together. The joining may also include hermetically sealing the feedthrough assembly 330, 1230, 1300 in the feedthrough port 320. For example, hermetically sealing the feedthrough assembly 330 in the feedthrough port 320 may include joining (e.g., welding) the feedthrough assembly 330, 1230, 1300 to the case 310 at the feedthrough port 320.

Based on the case representing a battery case, the method may optionally include one or more of connecting a first end of the inner conductor to one of the anode and the cathode, connecting a second end of the inner conductor to at least one of a circuitry or a processor of an implantable medical device, or disposing the memory, processor and the battery case in a housing of the implantable medical device. Additionally or alternatively, based on the case representing a housing for an IMD, the method may optionally include one or more of mounting a header to the housing proximate the feedthrough assembly, the header configured to be coupled to one or more leads, connecting a first end of the inner conductor to at least one of the circuitry or the processor, or connecting a second end of the inner conductor to at least one of an antenna or an electrode.

Accordingly, the present systems, devices, and methods provide for a feedthrough assembly that affords more reliable electrical connections to other battery and/or IMD components. Additionally or alternatively, the feedthrough assembly avoids damage to other components of the feedthrough assembly during joining operations to establish electrical connections.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

All references, including publications, patent applications and patents, cited herein are hereby incorporated by reference to the same extent as if each reference were individually and specifically indicated to be incorporated by reference and were set forth in its entirety herein.

What is claimed is:

1. An implantable medical device, comprising:
   memory configured to store program instructions;
   at least one of circuitry or a processor configured to execute the program instructions in connection with at least one of monitoring a biological signal or administering a therapy;
   a battery, comprising: a cell stack that includes an anode, a cathode, and one or more separator layers electrically insulating the anode from the cathode;
   a case having a feedthrough port; and
   a feedthrough assembly disposed in the feedthrough port, the feedthrough assembly including:
      a ferrule having a lumen;
      an inner conductor disposed within the lumen of the ferrule, the inner conductor formed from a first material having a first composition and a first coefficient of thermal expansion (CTE);
      an insulating core disposed within the lumen of the ferrule and separating the inner conductor from the ferrule, the insulating core formed from a second material having a second composition and a second CTE;
      wherein the first CTE of the inner conductor is greater than the second CTE of the insulating core; and
      wherein the first and second compositions are molecularly bonded with one another to form a hermetic seal between the inner conductor and the insulating core.

2. The device of claim 1, wherein the case represents a battery case, the battery case and feedthrough assembly hermetically enclosing the cell stack, the inner conductor having a first end connected to one of the anode and the cathode, the inner conductor having a second end connected to at least one of the circuitry or the processor, the device further comprising a housing that further encloses the memory, processor and the battery case.

3. The device of claim 1, wherein the case represents a housing for the implantable medical device, the case and feedthrough assembly hermetically enclosing the memory, the battery and at least one of the circuitry or the processor, the device further comprising a header configured to be coupled to one or more leads, the header mounted to the housing proximate the feedthrough assembly, the inner conductor having a first end connected to at least one of the circuitry or the processor, the inner conductor having a second end configured to be connected to at least one of an antenna or an electrode.

4. The device of claim 1, wherein the insulating core does not form a compression hermetic seal to the inner conductor due, at least in part, to the first CTE being greater than the second CTE.

5. The device of claim 1, wherein the first material forming the inner conductor has a melting point at or below 4500° F.

6. The device of claim 1, wherein the inner conductor is formed from at least one of titanium or niobium.

7. The device of claim 1, wherein the inner conductor and the ferrule are made of a common material.

8. The device of claim 1, wherein the first composition of the inner conductor represents an oxide based composition and the second composition of the insulating core represents an oxide based composition, wherein the molecular bond represents a chemical bond between the oxide based compositions of the first and second compositions to form the hermetic seal.

9. The device of claim 1, wherein the cathode includes a current collector disposed between cathode blanks, and wherein the current collector and the inner conductor are made of a common material.

10. The implantable medical device of claim 1, wherein the second composition of the insulating core contacts an outer surface of the inner conductor and reacts with the first composition of the inner conductor to form a glass-to-metal seal that hermetically seals the inner conductor to the insulating core.

11. A battery, comprising:
    a case having a feedthrough port;
    a cell stack disposed within the case, the cell stack including an anode, a cathode, and one or more separator layers electrically insulating the anode from the cathode,
    a feedthrough assembly disposed in the feedthrough port, the feedthrough assembly including:
       a ferrule having a lumen;
       an inner conductor disposed within the lumen of the ferrule, the inner conductor formed from a first material having a first composition and a first coefficient of thermal expansion (CTE);

an insulating core disposed within the lumen of the ferrule and separating the inner conductor from the ferrule, the insulating core formed from a second material having a second composition and a second CTE;

wherein the first CTE of the inner conductor is greater than the second CTE of the insulating core; and wherein the first and second compositions are molecularly bonded with one another to form a hermetic seal between the inner conductor and the insulating core.

12. The battery of claim 11, wherein the insulating core does not form a compression hermetic seal to the inner conductor due, at least in part, to the first CTE being greater than the second CTE.

13. The battery of claim 11, wherein the first material forming the inner conductor has a melting point at or below 4500° F.

14. The battery of claim 11, wherein the inner conductor is formed from at least one of titanium or niobium.

15. The battery of claim 11, wherein the inner conductor and the ferrule are made of a common material.

16. The battery of claim 11, wherein the first composition of the inner conductor represents an oxide based composition and the second composition of the insulating core represents an oxide based composition, wherein the molecular bond represents a chemical bond between the oxide based compositions of the first and second compositions to form the hermetic seal.

17. A method, comprising:
  disposing a cell stack within a case, the cell stack including an anode, a cathode, and one or more separator layers electrically insulating the anode from the cathode, the case having a feedthrough port;
  forming a feedthrough assembly that includes a ferrule having a lumen, the forming including:
    disposing an inner conductor within the lumen of the ferrule, the inner conductor formed from a first material having a first composition and a first coefficient of thermal expansion (CTE);
    disposing an insulating core within the lumen of the ferrule and separating the inner conductor from the ferrule, the insulating core formed from a second material having a second composition and a second CTE;
    wherein the first CTE of the inner conductor is greater than the second CTE of the insulating core; and
    wherein the first and second compositions are molecularly bonded with one another to form a hermetic seal between the inner conductor and the insulating core; and
  inserting the feedthrough assembly in the feedthrough port.

18. The method of claim 17, wherein the case represents a battery case, the battery case and feedthrough assembly hermetically enclosing the cell stack, and further comprising:
  connecting a first end of the inner conductor to one of the anode and the cathode;
  connecting a second end of the inner conductor to at least one of a circuitry or a processor of an implantable medical device; and
  disposing a memory, the processor and the battery case in a housing of the implantable medical device.

19. The method of claim 17, wherein the case represents a housing for an implantable medical device, the case and feedthrough assembly hermetically enclosing a memory, a battery and at least one of circuitry or a processor, and further comprising:
  mounting a header to the housing proximate the feedthrough assembly, the header configured to be coupled to one or more leads;
  connecting a first end of the inner conductor to at least one of the circuitry or the processor; and
  connecting a second end of the inner conductor to at least one of an antenna or an electrode.

20. The method of claim 17, wherein forming the feedthrough assembly further comprises forming the inner conductor and one or more of the ferrule and a current collector of the anode from a common material.

* * * * *